US010654911B1

(12) United States Patent
Li et al.

(10) Patent No.: US 10,654,911 B1
(45) Date of Patent: May 19, 2020

(54) VECTOR CO-EXPRESSING TRUNCATED VON WILLEBRAND FACTOR AND FACTOR VIII

(71) Applicant: Beijing Neoletix Biological Technology Co., Ltd., Beijing (CN)

(72) Inventors: Qi Li, Lawrenceville, GA (US); Hailong Zhang, Lilburn, GA (US)

(73) Assignee: Beijing Neoletix Biological Technology Co., Ltd., Beijing (CN)

( * ) Notice: Subject to any disclaimer, the term of this patent is extended or adjusted under 35 U.S.C. 154(b) by 0 days.

(21) Appl. No.: 16/373,511

(22) Filed: Apr. 2, 2019

(51) Int. Cl.
*A61K 38/36* (2006.01)
*C07K 14/755* (2006.01)

(52) U.S. Cl.
CPC ........ *C07K 14/755* (2013.01); *C07K 2319/02* (2013.01); *C07K 2319/30* (2013.01)

(58) Field of Classification Search
CPC ....... A61K 38/36; A61K 38/37; C07K 14/755
See application file for complete search history.

(56) References Cited

U.S. PATENT DOCUMENTS

| | | | | |
|---|---|---|---|---|
| 8,501,694 | B2 | 8/2013 | Lollar et al. | |
| 8,759,293 | B2 | 6/2014 | Barnett | |
| 10,138,291 | B2 | 11/2018 | Chhabra et al. | |
| 2015/0023959 | A1* | 1/2015 | Chhabra ................ | A61K 47/62 424/134.1 |

FOREIGN PATENT DOCUMENTS

| | | | |
|---|---|---|---|
| EP | 0253870 | B1 | 3/1993 |
| WO | 2014147386 | A1 | 9/2014 |
| WO | 2017117631 | A1 | 7/2017 |

OTHER PUBLICATIONS

S. Aguila, et al., "Novel therapies for hemophilia A—the role of the von Willebrand factor chaperone", Journal of Thrombosis and Haemostasis, 17:1-3, 2019.
Philip J. Fay, "Factor VIII Structure and Function", International Journal of Hematology 83 (2006) 103-108.
Randal J. Kaufman, et al., "Effect of von Willebrand Factor Coexpression on the Synthesis and Secretion of Factor VIII in Chinese Hamster Ovary Cells", Molecular and Cellular Biology, Mar. 1989, vol. 9, No. 3, p. 1233-1242.
Katherine J. Kearney, et al., "Affimer Proteins as a Tool to Modulate Fibrinolysis, Stabilize the Blood Clot and Reduce Bleeding Complications", Blood, 1st edition paper, Dec. 18, 2018.
Mille Petersen Kolind, et al., "Optimisation of the Factor VIII yield in mammalian cell cultures by reducing the membrane bound fraction", Journal of Biotechnology 151 (2011) 357-362.
Peter Lind, et al., "Novel forms of B-domain-deleted recombinant factor VIII molecules Construction and biochemical characterization", Eur. J. Biochem. 232, 19-27 (1995).
Sang Won Park, et al., "Long-Term Expression of von Willebrand Factor by a VSV-G Pseudotyped Lentivirus Enhances the Functional Activity of Secreted B-Domain-deleted Coagulation Factor VIII", Mol. Cells, vol. 24, No. 1, pp. 125-131 (2007).
Steven W. Pipe, et al., "Functional factor VIII made with von Willebrand factor at high levels in transgenic milk", J Thromb Haemost. Nov. 2011, 9(11): 2235-2242.
Angie R. Purvis, et al., "Two Cys residues essential for von Willebrand factor multimer assembly in the Golgi", PNAS, Oct. 2, 2007, vol. 104, No. 40, p. 15647-15652.
Nuha Shiltagh, et al., "Solution structure of the major factor VIII binding region on von Willebrand factor", Blood, Jun. 26, 2014, vol. 123, No. 26, p. 4143-4151.
Andrew Yee, et al., "A von Willebrand factor fragment containing the D'D3 domains is sufficient to stabilize coagulation factor VIII in mice", Blood, Jul. 17, 2004, vol. 124, No. 3.

* cited by examiner

*Primary Examiner* — Karen Cochrane Carlson
(74) *Attorney, Agent, or Firm* — Perkins Coie LLP; Viola T. Kung

(57) ABSTRACT

The present invention relates to a co-expression vector that comprises both truncated von Williebrand Factor (vWF)-Fc DNA construct and B-domain deleted FVIII DNA construct in the same vector. By co-expressing FVIII and truncated vWF-Fc with one expression vector in cells, the present invention controls the ratio of gene templates for FVIII and vWF proteins, provides a higher protein ratio of FVIII to vWF during cell expression, that results in a better occupancy of FVIII in vWF, and creates a higher yield (>1000 IU/ml) and more stable expression of FVIII protein molecules. In one preferred embodiment, the truncated vWF contains mutations of cysteines in the D'D3 domain of vWF to reduce multimer assembly of recombinant vWF during expression, and thus increasing recovery and quality of FVIII.

10 Claims, 11 Drawing Sheets

Specification includes a Sequence Listing.

SEQUENCE LISTING

<160> NUMBER OF SEQ ID NOS: 18

<210> SEQ ID NO 1
<211> LENGTH: 484
<212> TYPE: PRT
<213> ORGANISM: Homo sapiens

<400> SEQUENCE: 1

Ser Leu Ser Cys Arg Pro Pro Met Val Lys Leu Val Cys Pro Ala Asp
1 5 10 15

Asn Leu Arg Ala Glu Gly Leu Glu Cys Thr Lys Thr Cys Gln Asn Tyr
20 25 30

Asp Leu Glu Cys Met Ser Met Gly Cys Val Ser Gly Cys Leu Cys Pro
35 40 45

Pro Gly Met Val Arg His Glu Asn Arg Cys Val Ala Leu Glu Arg Cys

-continued

```
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Ala
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Ala Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480
```

-continued

Val Val Pro Pro

<210> SEQ ID NO 2
<211> LENGTH: 1225
<212> TYPE: PRT
<213> ORGANISM: Homo sapiens

<400> SEQUENCE: 2

Ala Glu Gly Thr Arg Gly Arg Ser Ser Thr Ala Arg Cys Ser Leu Phe
1               5                   10                  15

Gly Ser Asp Phe Val Asn Thr Phe Asp Gly Ser Met Tyr Ser Phe Ala
            20                  25                  30

Gly Tyr Cys Ser Tyr Leu Leu Ala Gly Gly Cys Gln Lys Arg Ser Phe
        35                  40                  45

Ser Ile Ile Gly Asp Phe Gln Asn Gly Lys Arg Val Ser Leu Ser Val
    50                  55                  60

Tyr Leu Gly Glu Phe Phe Asp Ile His Leu Phe Val Asn Gly Thr Val
65                  70                  75                  80

Thr Gln Gly Asp Gln Arg Val Ser Met Pro Tyr Ala Ser Lys Gly Leu
                85                  90                  95

Tyr Leu Glu Thr Glu Ala Gly Tyr Tyr Lys Leu Ser Gly Glu Ala Tyr
            100                 105                 110

Gly Phe Val Ala Arg Ile Asp Gly Ser Gly Asn Phe Gln Val Leu Leu
        115                 120                 125

Ser Asp Arg Tyr Phe Asn Lys Thr Cys Gly Leu Cys Gly Asn Phe Asn
    130                 135                 140

Ile Phe Ala Glu Asp Asp Phe Met Thr Gln Glu Gly Thr Leu Thr Ser
145                 150                 155                 160

Asp Pro Tyr Asp Phe Ala Asn Ser Trp Ala Leu Ser Ser Gly Glu Gln
                165                 170                 175

Trp Cys Glu Arg Ala Ser Pro Pro Ser Ser Ser Cys Asn Ile Ser Ser
            180                 185                 190

Gly Glu Met Gln Lys Gly Leu Trp Glu Gln Cys Gln Leu Leu Lys Ser
        195                 200                 205

Thr Ser Val Phe Ala Arg Cys His Pro Leu Val Asp Pro Glu Pro Phe
    210                 215                 220

Val Ala Leu Cys Glu Lys Thr Leu Cys Glu Cys Ala Gly Gly Leu Glu
225                 230                 235                 240

Cys Ala Cys Pro Ala Leu Leu Glu Tyr Ala Arg Thr Cys Ala Gln Glu
                245                 250                 255

Gly Met Val Leu Tyr Gly Trp Thr Asp His Ser Ala Cys Ser Pro Val
            260                 265                 270

Cys Pro Ala Gly Met Glu Tyr Arg Gln Cys Val Ser Pro Cys Ala Arg
        275                 280                 285

Thr Cys Gln Ser Leu His Ile Asn Glu Met Cys Gln Glu Arg Cys Val
    290                 295                 300

Asp Gly Cys Ser Cys Pro Glu Gly Gln Leu Leu Asp Glu Gly Leu Cys
305                 310                 315                 320

Val Glu Ser Thr Glu Cys Pro Cys Val His Ser Gly Lys Arg Tyr Pro
                325                 330                 335

Pro Gly Thr Ser Leu Ser Arg Asp Cys Asn Thr Cys Ile Cys Arg Asn
            340                 345                 350

Ser Gln Trp Ile Cys Ser Asn Glu Glu Cys Pro Gly Glu Cys Leu Val
        355                 360                 365

```
Thr Gly Gln Ser His Phe Lys Ser Phe Asp Asn Arg Tyr Phe Thr Phe
    370                 375                 380

Ser Gly Ile Cys Gln Tyr Leu Leu Ala Arg Asp Cys Gln Asp His Ser
385                 390                 395                 400

Phe Ser Ile Val Ile Glu Thr Val Gln Cys Ala Asp Asp Arg Asp Ala
                405                 410                 415

Val Cys Thr Arg Ser Val Thr Val Arg Leu Pro Gly Leu His Asn Ser
            420                 425                 430

Leu Val Lys Leu Lys His Gly Ala Gly Val Ala Met Asp Gly Gln Asp
        435                 440                 445

Ile Gln Leu Pro Leu Leu Lys Gly Asp Leu Arg Ile Gln His Thr Val
    450                 455                 460

Thr Ala Ser Val Arg Leu Ser Tyr Gly Glu Asp Leu Gln Met Asp Trp
465                 470                 475                 480

Asp Gly Arg Gly Arg Leu Leu Val Lys Leu Ser Pro Val Tyr Ala Gly
                485                 490                 495

Lys Thr Cys Gly Leu Cys Gly Asn Tyr Asn Gly Asn Gln Gly Asp Asp
            500                 505                 510

Phe Leu Thr Pro Ser Gly Leu Ala Glu Pro Arg Val Glu Asp Phe Gly
        515                 520                 525

Asn Ala Trp Lys Leu His Gly Asp Cys Gln Asp Leu Gln Lys Gln His
    530                 535                 540

Ser Asp Pro Cys Ala Leu Asn Pro Arg Met Thr Arg Phe Ser Glu Glu
545                 550                 555                 560

Ala Cys Ala Val Leu Thr Ser Pro Thr Phe Glu Ala Cys His Arg Ala
                565                 570                 575

Val Ser Pro Leu Pro Tyr Leu Arg Asn Cys Arg Tyr Asp Val Cys Ser
            580                 585                 590

Cys Ser Asp Gly Arg Glu Cys Leu Cys Gly Ala Leu Ala Ser Tyr Ala
        595                 600                 605

Ala Ala Cys Ala Gly Arg Gly Val Arg Val Ala Trp Arg Glu Pro Gly
    610                 615                 620

Arg Cys Glu Leu Asn Cys Pro Lys Gly Gln Val Tyr Leu Gln Cys Gly
625                 630                 635                 640

Thr Pro Cys Asn Leu Thr Cys Arg Ser Leu Ser Tyr Pro Asp Glu Glu
                645                 650                 655

Cys Asn Glu Ala Cys Leu Glu Gly Cys Phe Cys Pro Pro Gly Leu Tyr
            660                 665                 670

Met Asp Glu Arg Gly Asp Cys Val Pro Lys Ala Gln Cys Pro Cys Tyr
        675                 680                 685

Tyr Asp Gly Glu Ile Phe Gln Pro Glu Asp Ile Phe Ser Asp His His
    690                 695                 700

Thr Met Cys Tyr Cys Glu Asp Gly Phe Met His Cys Thr Met Ser Gly
705                 710                 715                 720

Val Pro Gly Ser Leu Leu Pro Asp Ala Val Leu Ser Ser Pro Leu Ser
                725                 730                 735

His Arg Ser Lys Arg Ser Leu Ser Cys Arg Pro Pro Met Val Lys Leu
            740                 745                 750

Val Cys Pro Ala Asp Asn Leu Arg Ala Glu Gly Leu Glu Cys Thr Lys
        755                 760                 765

Thr Cys Gln Asn Tyr Asp Leu Glu Cys Met Ser Met Gly Cys Val Ser
    770                 775                 780
```

-continued

```
Gly Cys Leu Cys Pro Pro Gly Met Val Arg His Glu Asn Arg Cys Val
785                 790                 795                 800

Ala Leu Glu Arg Cys Pro Cys Phe His Gln Gly Lys Glu Tyr Ala Pro
                805                 810                 815

Gly Glu Thr Val Lys Ile Gly Cys Asn Thr Cys Val Cys Arg Asp Arg
            820                 825                 830

Lys Trp Asn Cys Thr Asp His Val Cys Asp Ala Thr Cys Ser Thr Ile
        835                 840                 845

Gly Met Ala His Tyr Leu Thr Phe Asp Gly Leu Lys Tyr Leu Phe Pro
    850                 855                 860

Gly Glu Cys Gln Tyr Val Leu Val Gln Asp Tyr Cys Gly Ser Asn Pro
865                 870                 875                 880

Gly Thr Phe Arg Ile Leu Val Gly Asn Lys Gly Cys Ser His Pro Ser
                885                 890                 895

Val Lys Cys Lys Lys Arg Val Thr Ile Leu Val Glu Gly Gly Glu Ile
            900                 905                 910

Glu Leu Phe Asp Gly Glu Val Asn Val Lys Arg Pro Met Lys Asp Glu
        915                 920                 925

Thr His Phe Glu Val Val Glu Ser Gly Arg Tyr Ile Ile Leu Leu Leu
    930                 935                 940

Gly Lys Ala Leu Ser Val Val Trp Asp Arg His Leu Ser Ile Ser Val
945                 950                 955                 960

Val Leu Lys Gln Thr Tyr Gln Glu Lys Val Cys Gly Leu Cys Gly Asn
                965                 970                 975

Phe Asp Gly Ile Gln Asn Asn Asp Leu Thr Ser Ser Asn Leu Gln Val
            980                 985                 990

Glu Glu Asp Pro Val Asp Phe Gly  Asn Ser Trp Lys Val  Ser Ser Gln
        995                 1000                 1005

Cys Ala  Asp Thr Arg Lys Val  Pro Leu Asp Ser Ser  Pro Ala Thr
    1010                 1015                 1020

Cys His  Asn Asn Ile Met Lys  Gln Thr Met Val Asp  Ser Ser Cys
    1025                 1030                 1035

Arg Ile  Leu Thr Ser Asp Val  Phe Gln Asp Cys Asn  Lys Leu Val
    1040                 1045                 1050

Asp Pro  Glu Pro Tyr Leu Asp  Val Cys Ile Tyr Asp  Thr Cys Ser
    1055                 1060                 1065

Cys Glu  Ser Ile Gly Asp Cys  Ala Ala Phe Cys Asp  Thr Ile Ala
    1070                 1075                 1080

Ala Tyr  Ala His Val Cys Ala  Gln His Gly Lys Val  Val Thr Trp
    1085                 1090                 1095

Arg Thr  Ala Thr Leu Cys Pro  Gln Ser Cys Glu Glu  Arg Asn Leu
    1100                 1105                 1110

Arg Glu  Asn Gly Tyr Glu Ala  Glu Trp Arg Tyr Asn  Ser Cys Ala
    1115                 1120                 1125

Pro Ala  Cys Gln Val Thr Cys  Gln His Pro Glu Pro  Leu Ala Cys
    1130                 1135                 1140

Pro Val  Gln Cys Val Glu Gly  Cys His Ala His Cys  Pro Pro Gly
    1145                 1150                 1155

Lys Ile  Leu Asp Glu Leu Leu  Gln Thr Cys Val Asp  Pro Glu Asp
    1160                 1165                 1170

Cys Pro  Val Cys Glu Val Ala  Gly Arg Arg Phe Ala  Ser Gly Lys
    1175                 1180                 1185

Lys Val  Thr Leu Asn Pro Ser  Asp Pro Glu His Cys  Gln Ile Cys
```

-continued

```
    1190                1195                1200

His Cys  Asp Val Val Asn Leu  Thr Cys Glu Ala Cys  Gln Glu Pro
    1205                1210                1215

Gly Gly  Leu Val Val Pro Pro
    1220                1225


<210> SEQ ID NO 3
<211> LENGTH: 484
<212> TYPE: PRT
<213> ORGANISM: Homo sapiens

<400> SEQUENCE: 3

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335
```

-continued

Phe Cys Asp Thr Ile Ala Ala Tyr Ala His Val Cys Ala Gln His Gly
340 345 350

Lys Val Val Thr Trp Arg Thr Ala Thr Leu Cys Pro Gln Ser Cys Glu
355 360 365

Glu Arg Asn Leu Arg Glu Asn Gly Tyr Glu Cys Glu Trp Arg Tyr Asn
370 375 380

Ser Cys Ala Pro Ala Cys Gln Val Thr Cys Gln His Pro Glu Pro Leu
385 390 395 400

Ala Cys Pro Val Gln Cys Val Glu Gly Cys His Ala His Cys Pro Pro
405 410 415

Gly Lys Ile Leu Asp Glu Leu Leu Gln Thr Cys Val Asp Pro Glu Asp
420 425 430

Cys Pro Val Cys Glu Val Ala Gly Arg Arg Phe Ala Ser Gly Lys Lys
435 440 445

Val Thr Leu Asn Pro Ser Asp Pro Glu His Cys Gln Ile Cys His Cys
450 455 460

Asp Val Val Asn Leu Thr Cys Glu Ala Cys Gln Glu Pro Gly Gly Leu
465 470 475 480

Val Val Pro Pro

<210> SEQ ID NO 4
<211> LENGTH: 1225
<212> TYPE: PRT
<213> ORGANISM: Homo sapiens

<400> SEQUENCE: 4

Ala Glu Gly Thr Arg Gly Arg Ser Ser Thr Ala Arg Cys Ser Leu Phe
1 5 10 15

Gly Ser Asp Phe Val Asn Thr Phe Asp Gly Ser Met Tyr Ser Phe Ala
20 25 30

Gly Tyr Cys Ser Tyr Leu Leu Ala Gly Gly Cys Gln Lys Arg Ser Phe
35 40 45

Ser Ile Ile Gly Asp Phe Gln Asn Gly Lys Arg Val Ser Leu Ser Val
50 55 60

Tyr Leu Gly Glu Phe Phe Asp Ile His Leu Phe Val Asn Gly Thr Val
65 70 75 80

Thr Gln Gly Asp Gln Arg Val Ser Met Pro Tyr Ala Ser Lys Gly Leu
85 90 95

Tyr Leu Glu Thr Glu Ala Gly Tyr Tyr Lys Leu Ser Gly Glu Ala Tyr
100 105 110

Gly Phe Val Ala Arg Ile Asp Gly Ser Gly Asn Phe Gln Val Leu Leu
115 120 125

Ser Asp Arg Tyr Phe Asn Lys Thr Cys Gly Leu Cys Gly Asn Phe Asn
130 135 140

Ile Phe Ala Glu Asp Asp Phe Met Thr Gln Glu Gly Thr Leu Thr Ser
145 150 155 160

Asp Pro Tyr Asp Phe Ala Asn Ser Trp Ala Leu Ser Ser Gly Glu Gln
165 170 175

Trp Cys Glu Arg Ala Ser Pro Pro Ser Ser Ser Cys Asn Ile Ser Ser
180 185 190

Gly Glu Met Gln Lys Gly Leu Trp Glu Gln Cys Gln Leu Leu Lys Ser
195 200 205

Thr Ser Val Phe Ala Arg Cys His Pro Leu Val Asp Pro Glu Pro Phe
210 215 220

-continued

```
Val Ala Leu Cys Glu Lys Thr Leu Cys Glu Cys Ala Gly Gly Leu Glu
225                 230                 235                 240

Cys Ala Cys Pro Ala Leu Leu Glu Tyr Ala Arg Thr Cys Ala Gln Glu
                245                 250                 255

Gly Met Val Leu Tyr Gly Trp Thr Asp His Ser Ala Cys Ser Pro Val
            260                 265                 270

Cys Pro Ala Gly Met Glu Tyr Arg Gln Cys Val Ser Pro Cys Ala Arg
        275                 280                 285

Thr Cys Gln Ser Leu His Ile Asn Glu Met Cys Gln Glu Arg Cys Val
    290                 295                 300

Asp Gly Cys Ser Cys Pro Glu Gly Gln Leu Leu Asp Glu Gly Leu Cys
305                 310                 315                 320

Val Glu Ser Thr Glu Cys Pro Cys Val His Ser Gly Lys Arg Tyr Pro
                325                 330                 335

Pro Gly Thr Ser Leu Ser Arg Asp Cys Asn Thr Cys Ile Cys Arg Asn
            340                 345                 350

Ser Gln Trp Ile Cys Ser Asn Glu Glu Cys Pro Gly Glu Cys Leu Val
        355                 360                 365

Thr Gly Gln Ser His Phe Lys Ser Phe Asp Asn Arg Tyr Phe Thr Phe
    370                 375                 380

Ser Gly Ile Cys Gln Tyr Leu Leu Ala Arg Asp Cys Gln Asp His Ser
385                 390                 395                 400

Phe Ser Ile Val Ile Glu Thr Val Gln Cys Ala Asp Asp Arg Asp Ala
                405                 410                 415

Val Cys Thr Arg Ser Val Thr Val Arg Leu Pro Gly Leu His Asn Ser
            420                 425                 430

Leu Val Lys Leu Lys His Gly Ala Gly Val Ala Met Asp Gly Gln Asp
        435                 440                 445

Ile Gln Leu Pro Leu Leu Lys Gly Asp Leu Arg Ile Gln His Thr Val
    450                 455                 460

Thr Ala Ser Val Arg Leu Ser Tyr Gly Glu Asp Leu Gln Met Asp Trp
465                 470                 475                 480

Asp Gly Arg Gly Arg Leu Leu Val Lys Leu Ser Pro Val Tyr Ala Gly
                485                 490                 495

Lys Thr Cys Gly Leu Cys Gly Asn Tyr Asn Gly Asn Gln Gly Asp Asp
            500                 505                 510

Phe Leu Thr Pro Ser Gly Leu Ala Glu Pro Arg Val Glu Asp Phe Gly
        515                 520                 525

Asn Ala Trp Lys Leu His Gly Asp Cys Gln Asp Leu Gln Lys Gln His
    530                 535                 540

Ser Asp Pro Cys Ala Leu Asn Pro Arg Met Thr Arg Phe Ser Glu Glu
545                 550                 555                 560

Ala Cys Ala Val Leu Thr Ser Pro Thr Phe Glu Ala Cys His Arg Ala
                565                 570                 575

Val Ser Pro Leu Pro Tyr Leu Arg Asn Cys Arg Tyr Asp Val Cys Ser
            580                 585                 590

Cys Ser Asp Gly Arg Glu Cys Leu Cys Gly Ala Leu Ala Ser Tyr Ala
        595                 600                 605

Ala Ala Cys Ala Gly Arg Gly Val Arg Val Ala Trp Arg Glu Pro Gly
    610                 615                 620

Arg Cys Glu Leu Asn Cys Pro Lys Gly Gln Val Tyr Leu Gln Cys Gly
625                 630                 635                 640

Thr Pro Cys Asn Leu Thr Cys Arg Ser Leu Ser Tyr Pro Asp Glu Glu
```

-continued

```
                645                 650                 655

Cys Asn Glu Ala Cys Leu Glu Gly Cys Phe Cys Pro Pro Gly Leu Tyr
            660                 665                 670

Met Asp Glu Arg Gly Asp Cys Val Pro Lys Ala Gln Cys Pro Cys Tyr
        675                 680                 685

Tyr Asp Gly Glu Ile Phe Gln Pro Glu Asp Ile Phe Ser Asp His His
    690                 695                 700

Thr Met Cys Tyr Cys Glu Asp Gly Phe Met His Cys Thr Met Ser Gly
705                 710                 715                 720

Val Pro Gly Ser Leu Leu Pro Asp Ala Val Leu Ser Ser Pro Leu Ser
                725                 730                 735

His Arg Ser Lys Arg Ser Leu Ser Cys Arg Pro Pro Met Val Lys Leu
            740                 745                 750

Val Cys Pro Ala Asp Asn Leu Arg Ala Glu Gly Leu Glu Cys Thr Lys
        755                 760                 765

Thr Cys Gln Asn Tyr Asp Leu Glu Cys Met Ser Met Gly Cys Val Ser
    770                 775                 780

Gly Cys Leu Cys Pro Pro Gly Met Val Arg His Glu Asn Arg Cys Val
785                 790                 795                 800

Ala Leu Glu Arg Cys Pro Cys Phe His Gln Gly Lys Glu Tyr Ala Pro
                805                 810                 815

Gly Glu Thr Val Lys Ile Gly Cys Asn Thr Cys Val Cys Arg Asp Arg
            820                 825                 830

Lys Trp Asn Cys Thr Asp His Val Cys Asp Ala Thr Cys Ser Thr Ile
        835                 840                 845

Gly Met Ala His Tyr Leu Thr Phe Asp Gly Leu Lys Tyr Leu Phe Pro
    850                 855                 860

Gly Glu Cys Gln Tyr Val Leu Val Gln Asp Tyr Cys Gly Ser Asn Pro
865                 870                 875                 880

Gly Thr Phe Arg Ile Leu Val Gly Asn Lys Gly Cys Ser His Pro Ser
                885                 890                 895

Val Lys Cys Lys Lys Arg Val Thr Ile Leu Val Glu Gly Gly Glu Ile
            900                 905                 910

Glu Leu Phe Asp Gly Glu Val Asn Val Lys Arg Pro Met Lys Asp Glu
        915                 920                 925

Thr His Phe Glu Val Val Glu Ser Gly Arg Tyr Ile Ile Leu Leu Leu
    930                 935                 940

Gly Lys Ala Leu Ser Val Val Trp Asp Arg His Leu Ser Ile Ser Val
945                 950                 955                 960

Val Leu Lys Gln Thr Tyr Gln Glu Lys Val Cys Gly Leu Cys Gly Asn
                965                 970                 975

Phe Asp Gly Ile Gln Asn Asn Asp Leu Thr Ser Ser Asn Leu Gln Val
            980                 985                 990

Glu Glu Asp Pro Val Asp Phe Gly  Asn Ser Trp Lys Val  Ser Ser Gln
        995                 1000                1005

Cys Ala  Asp Thr Arg Lys Val  Pro Leu Asp Ser Ser  Pro Ala Thr
    1010                1015                1020

Cys His  Asn Asn Ile Met Lys  Gln Thr Met Val Asp  Ser Ser Cys
    1025                1030                1035

Arg Ile  Leu Thr Ser Asp Val  Phe Gln Asp Cys Asn  Lys Leu Val
    1040                1045                1050

Asp Pro  Glu Pro Tyr Leu Asp  Val Cys Ile Tyr Asp  Thr Cys Ser
    1055                1060                1065
```

```
Cys Glu  Ser Ile Gly Asp Cys  Ala Cys Phe Cys Asp  Thr Ile Ala
    1070                 1075                 1080

Ala Tyr  Ala His Val Cys Ala  Gln His Gly Lys Val  Val Thr Trp
    1085                 1090                 1095

Arg Thr  Ala Thr Leu Cys Pro  Gln Ser Cys Glu Glu  Arg Asn Leu
    1100                 1105                 1110

Arg Glu  Asn Gly Tyr Glu Cys  Glu Trp Arg Tyr Asn  Ser Cys Ala
    1115                 1120                 1125

Pro Ala  Cys Gln Val Thr Cys  Gln His Pro Glu Pro  Leu Ala Cys
    1130                 1135                 1140

Pro Val  Gln Cys Val Glu Gly  Cys His Ala His Cys  Pro Pro Gly
    1145                 1150                 1155

Lys Ile  Leu Asp Glu Leu Leu  Gln Thr Cys Val Asp  Pro Glu Asp
    1160                 1165                 1170

Cys Pro  Val Cys Glu Val Ala  Gly Arg Arg Phe Ala  Ser Gly Lys
    1175                 1180                 1185

Lys Val  Thr Leu Asn Pro Ser  Asp Pro Glu His Cys  Gln Ile Cys
    1190                 1195                 1200

His Cys  Asp Val Val Asn Leu  Thr Cys Glu Ala Cys  Gln Glu Pro
    1205                 1210                 1215

Gly Gly  Leu Val Val Pro Pro
    1220                 1225


<210> SEQ ID NO 5
<211> LENGTH: 227
<212> TYPE: PRT
<213> ORGANISM: Homo sapiens

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
```

```
        195                 200                 205

His Glu Ala Leu His Asn His Tyr Thr Gln Lys Ser Leu Ser Leu Ser
    210                 215                 220

Pro Gly Lys
225


<210> SEQ ID NO 6
<211> LENGTH: 1438
<212> TYPE: PRT
<213> ORGANISM: Homo sapiens

<400> SEQUENCE: 6

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335
```

-continued

```
Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
```

-continued

```
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn  Met Glu Arg Asn Cys  Arg Ala Pro
        995                 1000                1005

Cys Asn  Ile Gln Met Glu Asp  Pro Thr Phe Lys Glu  Asn Tyr Arg
    1010                1015                1020

Phe His  Ala Ile Asn Gly Tyr  Ile Met Asp Thr Leu  Pro Gly Leu
    1025                1030                1035

Val Met  Ala Gln Asp Gln Arg  Ile Arg Trp Tyr Leu  Leu Ser Met
    1040                1045                1050

Gly Ser  Asn Glu Asn Ile His  Ser Ile His Phe Ser  Gly His Val
    1055                1060                1065

Phe Thr  Val Arg Lys Lys Glu  Glu Tyr Lys Met Ala  Leu Tyr Asn
    1070                1075                1080

Leu Tyr  Pro Gly Val Phe Glu  Thr Val Glu Met Leu  Pro Ser Lys
    1085                1090                1095

Ala Gly  Ile Trp Arg Val Glu  Cys Leu Ile Gly Glu  His Leu His
    1100                1105                1110

Ala Gly  Met Ser Thr Leu Phe  Leu Val Tyr Ser Asn  Lys Cys Gln
    1115                1120                1125

Thr Pro  Leu Gly Met Ala Ser  Gly His Ile Arg Asp  Phe Gln Ile
    1130                1135                1140

Thr Ala  Ser Gly Gln Tyr Gly  Gln Trp Ala Pro Lys  Leu Ala Arg
    1145                1150                1155

Leu His  Tyr Ser Gly Ser Ile  Asn Ala Trp Ser Thr  Lys Glu Pro
    1160                1165                1170
```

```
Phe Ser  Trp Ile Lys Val Asp  Leu Leu Ala Pro Met  Ile Ile His
    1175                 1180                 1185

Gly Ile  Lys Thr Gln Gly Ala  Arg Gln Lys Phe Ser  Ser Leu Tyr
    1190                 1195                 1200

Ile Ser  Gln Phe Ile Ile Met  Tyr Ser Leu Asp Gly  Lys Lys Trp
    1205                 1210                 1215

Gln Thr  Tyr Arg Gly Asn Ser  Thr Gly Thr Leu Met  Val Phe Phe
    1220                 1225                 1230

Gly Asn  Val Asp Ser Ser Gly  Ile Lys His Asn Ile  Phe Asn Pro
    1235                 1240                 1245

Pro Ile  Ile Ala Arg Tyr Ile  Arg Leu His Pro Thr  His Tyr Ser
    1250                 1255                 1260

Ile Arg  Ser Thr Leu Arg Met  Glu Leu Met Gly Cys  Asp Leu Asn
    1265                 1270                 1275

Ser Cys  Ser Met Pro Leu Gly  Met Glu Ser Lys Ala  Ile Ser Asp
    1280                 1285                 1290

Ala Gln  Ile Thr Ala Ser Ser  Tyr Phe Thr Asn Met  Phe Ala Thr
    1295                 1300                 1305

Trp Ser  Pro Ser Lys Ala Arg  Leu His Leu Gln Gly  Arg Ser Asn
    1310                 1315                 1320

Ala Trp  Arg Pro Gln Val Asn  Asn Pro Lys Glu Trp  Leu Gln Val
    1325                 1330                 1335

Asp Phe  Gln Lys Thr Met Lys  Val Thr Gly Val Thr  Thr Gln Gly
    1340                 1345                 1350

Val Lys  Ser Leu Leu Thr Ser  Met Tyr Val Lys Glu  Phe Leu Ile
    1355                 1360                 1365

Ser Ser  Ser Gln Asp Gly His  Gln Trp Thr Leu Phe  Phe Gln Asn
    1370                 1375                 1380

Gly Lys  Val Lys Val Phe Gln  Gly Asn Gln Asp Ser  Phe Thr Pro
    1385                 1390                 1395

Val Val  Asn Ser Leu Asp Pro  Pro Leu Leu Thr Arg  Tyr Leu Arg
    1400                 1405                 1410

Ile His  Pro Gln Ser Trp Val  His Gln Ile Ala Leu  Arg Met Glu
    1415                 1420                 1425

Val Leu  Gly Cys Glu Ala Gln  Asp Leu Tyr
    1430                 1435


<210> SEQ ID NO 7
<211> LENGTH: 1448
<212> TYPE: PRT
<213> ORGANISM: Porcine

<400> SEQUENCE: 7

Ala Ile Arg Arg Tyr Tyr Leu Gly Ala Val Glu Leu Ser Trp Asp Tyr
1               5                   10                  15

Arg Gln Ser Glu Leu Leu Arg Glu Leu His Val Asp Thr Arg Phe Pro
            20                  25                  30

Ala Thr Ala Pro Gly Ala Leu Pro Leu Gly Pro Ser Val Leu Tyr Lys
        35                  40                  45

Lys Thr Val Phe Val Glu Phe Thr Asp Gln Leu Phe Ser Val Ala Arg
    50                  55                  60

Pro Arg Pro Pro Trp Met Gly Leu Leu Gly Pro Thr Ile Gln Ala Glu
65                  70                  75                  80

Val Tyr Asp Thr Val Val Val Thr Leu Lys Asn Met Ala Ser His Pro
```

-continued

```
                85                  90                  95

Val Ser Leu His Ala Val Gly Val Ser Phe Trp Lys Ser Ser Glu Gly
            100                 105                 110

Ala Glu Tyr Glu Asp His Thr Ser Gln Arg Glu Lys Glu Asp Asp Lys
        115                 120                 125

Val Leu Pro Gly Lys Ser Gln Thr Tyr Val Trp Gln Val Leu Lys Glu
    130                 135                 140

Asn Gly Pro Thr Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Arg Glu Gly Ser Leu Thr Arg Glu Arg Thr Gln Asn
            180                 185                 190

Leu His Glu Phe Val Leu Leu Phe Ala Val Phe Asp Glu Gly Lys Ser
        195                 200                 205

Trp His Ser Ala Arg Asn Asp Ser Trp Thr Arg Ala Met Asp Pro Ala
    210                 215                 220

Pro Ala Arg Ala Gln Pro Ala Met His Thr Val Asn Gly Tyr Val Asn
225                 230                 235                 240

Arg Ser Leu Pro Gly Leu Ile Gly Cys His Lys Lys Ser Val Tyr Trp
                245                 250                 255

His Val Ile Gly Met Gly Thr Ser Pro Glu Val His Ser Ile Phe Leu
            260                 265                 270

Glu Gly His Thr Phe Leu Val Arg His His Arg Gln Ala Ser Leu Glu
        275                 280                 285

Ile Ser Pro Leu Thr Phe Leu Thr Ala Gln Thr Phe Leu Met Asp Leu
    290                 295                 300

Gly Gln Phe Leu Leu Phe Cys His Ile Ser Ser His His His Gly Gly
305                 310                 315                 320

Met Glu Ala His Val Arg Val Glu Ser Cys Ala Glu Glu Pro Gln Leu
                325                 330                 335

Arg Arg Lys Ala Asp Glu Glu Glu Asp Tyr Asp Asp Asn Leu Tyr Asp
            340                 345                 350

Ser Asp Met Asp Val Val Arg Leu Asp Gly Asp Asp Val Ser Pro Phe
        355                 360                 365

Ile Gln Ile Arg Ser Val Ala Lys Lys His Pro Lys Thr Trp Val His
    370                 375                 380

Tyr Ile Ser Ala Glu Glu Glu Asp Trp Asp Tyr Ala Pro Ala Val Pro
385                 390                 395                 400

Ser Pro Ser Asp Arg Ser Tyr Lys Ser Leu Tyr Leu Asn Ser Gly Pro
                405                 410                 415

Gln Arg Ile Gly Arg Lys Tyr Lys Lys Ala Arg Phe Val Ala Tyr Thr
            420                 425                 430

Asp Val Thr Phe Lys Thr Arg Lys Ala Ile Pro Tyr Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Lys Ala Ser Arg Pro Tyr Asn Ile Tyr Pro His Gly Ile
465                 470                 475                 480

Thr Asp Val Ser Ala Leu His Pro Gly Arg Leu Leu Lys Gly Trp Lys
                485                 490                 495

His Leu Lys Asp Met Pro Ile Leu Pro Gly Glu Thr Phe Lys Tyr Lys
            500                 505                 510
```

```
Trp Thr Val Thr Val Glu Asp Gly Pro Thr Lys Ser Asp Pro Arg Cys
        515                 520                 525

Leu Thr Arg Tyr Tyr Ser Ser Ser Ile Asn Leu Glu Lys Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Met Met Ser Asp Lys Arg Asn Val Ile Leu Phe
                565                 570                 575

Ser Val Phe Asp Glu Asn Gln Ser Trp Tyr Leu Ala Glu Asn Ile Gln
            580                 585                 590

Arg Phe Leu Pro Asn Pro Asp Gly Leu Gln Pro Gln Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Val Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Val Leu Gly Cys His Asn Ser Asp Leu Arg Asn Arg Gly Met Thr Ala
    690                 695                 700

Leu Leu Lys Val Tyr Ser Cys Asp Arg Asp Ile Gly Asp Tyr Tyr Asp
705                 710                 715                 720

Asn Thr Tyr Glu Asp Ile Pro Gly Phe Leu Leu Ser Gly Lys Asn Val
                725                 730                 735

Ile Glu Pro Arg Ser Phe Ala Gln Asn Ser Arg Pro Pro Ser Ala Ser
            740                 745                 750

Ala Pro Lys Pro Pro Val Leu Arg Arg His Gln Arg Asp Ile Ser Leu
        755                 760                 765

Pro Thr Phe Gln Pro Glu Glu Asp Lys Met Asp Tyr Asp Asp Ile Phe
    770                 775                 780

Ser Thr Glu Thr Lys Gly Glu Asp Phe Asp Ile Tyr Gly Glu Asp Glu
785                 790                 795                 800

Asn Gln Asp Pro Arg Ser Phe Gln Lys Arg Thr Arg His Tyr Phe Ile
                805                 810                 815

Ala Ala Val Glu Gln Leu Trp Asp Tyr Gly Met Ser Glu Ser Pro Arg
            820                 825                 830

Ala Leu Arg Asn Arg Ala Gln Asn Gly Glu Val Pro Arg Phe Lys Lys
        835                 840                 845

Val Val Phe Arg Glu Phe Ala Asp Gly Ser Phe Thr Gln Pro Ser Tyr
    850                 855                 860

Arg Gly Glu Leu Asn Lys His Leu Gly Leu Leu Gly Pro Tyr Ile Arg
865                 870                 875                 880

Ala Glu Val Glu Asp Asn Ile Met Val Thr Phe Lys Asn Gln Ala Ser
                885                 890                 895

Arg Pro Tyr Ser Phe Tyr Ser Ser Leu Ile Ser Tyr Pro Asp Asp Gln
            900                 905                 910

Glu Gln Gly Ala Glu Pro Arg His Asn Phe Val Gln Pro Asn Glu Thr
        915                 920                 925
```

-continued

```
Arg Thr Tyr Phe Trp Lys Val Gln His His Met Ala Pro Thr Glu Asp
    930                 935                 940

Glu Phe Asp Cys Lys Ala Trp Ala Tyr Phe Ser Asp Val Asp Leu Glu
945                 950                 955                 960

Lys Asp Val His Ser Gly Leu Ile Gly Pro Leu Leu Ile Cys Arg Ala
                965                 970                 975

Asn Thr Leu Asn Ala Ala His Gly Arg Gln Val Thr Val Gln Glu Phe
            980                 985                 990

Ala Leu Phe Phe Thr Ile Phe Asp  Glu Thr Lys Ser Trp  Tyr Phe Thr
        995                 1000                 1005

Glu Asn  Val Glu Arg Asn Cys  Arg Ala Pro Cys His  Leu Gln Met
    1010                 1015                 1020

Glu Asp  Pro Thr Leu Lys Glu  Asn Tyr Arg Phe His  Ala Ile Asn
    1025                 1030                 1035

Gly Tyr  Val Met Asp Thr Leu  Pro Gly Leu Val Met  Ala Gln Asn
    1040                 1045                 1050

Gln Arg  Ile Arg Trp Tyr Leu  Leu Ser Met Gly Ser  Asn Glu Asn
    1055                 1060                 1065

Ile His  Ser Ile His Phe Ser  Gly His Val Phe Ser  Val Arg Lys
    1070                 1075                 1080

Lys Glu  Glu Tyr Lys Met Ala  Val Tyr Asn Leu Tyr  Pro Gly Val
    1085                 1090                 1095

Phe Glu  Thr Val Glu Met Leu  Pro Ser Lys Val Gly  Ile Trp Arg
    1100                 1105                 1110

Ile Glu  Cys Leu Ile Gly Glu  His Leu Gln Ala Gly  Met Ser Thr
    1115                 1120                 1125

Thr Phe  Leu Val Tyr Ser Lys  Glu Cys Gln Ala Pro  Leu Gly Met
    1130                 1135                 1140

Ala Ser  Gly Arg Ile Arg Asp  Phe Gln Ile Thr Ala  Ser Gly Gln
    1145                 1150                 1155

Tyr Gly  Gln Trp Ala Pro Lys  Leu Ala Arg Leu His  Tyr Ser Gly
    1160                 1165                 1170

Ser Ile  Asn Ala Trp Ser Thr  Lys Asp Pro His Ser  Trp Ile Lys
    1175                 1180                 1185

Val Asp  Leu Leu Ala Pro Met  Ile Ile His Gly Ile  Met Thr Gln
    1190                 1195                 1200

Gly Ala  Arg Gln Lys Phe Ser  Ser Leu Tyr Ile Ser  Gln Phe Ile
    1205                 1210                 1215

Ile Met  Tyr Ser Leu Asp Gly  Arg Asn Trp Gln Ser  Tyr Arg Gly
    1220                 1225                 1230

Asn Ser  Thr Gly Thr Leu Met  Val Phe Phe Gly Asn  Val Asp Ala
    1235                 1240                 1245

Ser Gly  Ile Lys His Asn Ile  Phe Asn Pro Pro Ile  Val Ala Arg
    1250                 1255                 1260

Tyr Ile  Arg Leu His Pro Thr  His Tyr Ser Ile Arg  Ser Thr Leu
    1265                 1270                 1275

Arg Met  Glu Leu Met Gly Cys  Asp Leu Asn Ser Cys  Ser Met Pro
    1280                 1285                 1290

Leu Gly  Met Gln Asn Lys Ala  Ile Ser Asp Ser Gln  Ile Thr Ala
    1295                 1300                 1305

Ser Ser  His Leu Ser Asn Ile  Phe Ala Thr Trp Ser  Pro Ser Gln
    1310                 1315                 1320

Ala Arg  Leu His Leu Gln Gly  Arg Thr Asn Ala Trp  Arg Pro Arg
```

-continued

```
    1325                1330                1335

Val Ser  Ser Ala Glu Glu Trp  Leu Gln Val Asp Leu  Gln Lys Thr
    1340                1345                1350

Val Lys  Val Thr Gly Ile Thr  Thr Gln Gly Val Lys  Ser Leu Leu
    1355                1360                1365

Ser Ser  Met Tyr Val Lys Glu  Phe Leu Val Ser Ser  Ser Gln Asp
    1370                1375                1380

Gly Arg  Arg Trp Thr Leu Phe  Leu Gln Asp Gly His  Thr Lys Val
    1385                1390                1395

Phe Gln  Gly Asn Gln Asp Ser  Ser Thr Pro Val Val  Asn Ala Leu
    1400                1405                1410

Asp Pro  Pro Leu Phe Thr Arg  Tyr Leu Arg Ile His  Pro Thr Ser
    1415                1420                1425

Trp Ala  Gln His Ile Ala Leu  Arg Leu Glu Val Leu  Gly Cys Glu
    1430                1435                1440

Ala Gln  Asp Leu Tyr
    1445


<210> SEQ ID NO 8
<211> LENGTH: 1438
<212> TYPE: PRT
<213> ORGANISM: Porcine

<400> SEQUENCE: 8

Ala Ile Arg Arg Tyr Tyr Leu Gly Ala Val Glu Leu Ser Trp Asp Tyr
1               5                   10                  15

Arg Gln Ser Glu Leu Leu Arg Glu Leu His Val Asp Thr Arg Phe Pro
            20                  25                  30

Ala Thr Ala Pro Gly Ala Leu Pro Leu Gly Pro Ser Val Leu Tyr Lys
        35                  40                  45

Lys Thr Val Phe Val Glu Phe Thr Asp Gln Leu Phe Ser Val Ala Arg
    50                  55                  60

Pro Arg Pro Pro Trp Met Gly Leu Leu Gly Pro Thr Ile Gln Ala Glu
65                  70                  75                  80

Val Tyr Asp Thr Val Val Val Thr Leu Lys Asn Met Ala Ser His Pro
                85                  90                  95

Val Ser Leu His Ala Val Gly Val Ser Phe Trp Lys Ser Ser Glu Gly
            100                 105                 110

Ala Glu Tyr Glu Asp His Thr Ser Gln Arg Glu Lys Glu Asp Asp Lys
        115                 120                 125

Val Leu Pro Gly Lys Ser Gln Thr Tyr Val Trp Gln Val Leu Lys Glu
    130                 135                 140

Asn Gly Pro Thr Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Arg Glu Gly Ser Leu Thr Arg Glu Arg Thr Gln Asn
            180                 185                 190

Leu His Glu Phe Val Leu Leu Phe Ala Val Phe Asp Glu Gly Lys Ser
        195                 200                 205

Trp His Ser Ala Arg Asn Asp Ser Trp Thr Arg Ala Met Asp Pro Ala
    210                 215                 220

Pro Ala Arg Ala Gln Pro Ala Met His Thr Val Asn Gly Tyr Val Asn
225                 230                 235                 240
```

-continued

```
Arg Ser Leu Pro Gly Leu Ile Gly Cys His Lys Lys Ser Val Tyr Trp
                245                 250                 255

His Val Ile Gly Met Gly Thr Ser Pro Glu Val His Ser Ile Phe Leu
            260                 265                 270

Glu Gly His Thr Phe Leu Val Arg His His Arg Gln Ala Ser Leu Glu
        275                 280                 285

Ile Ser Pro Leu Thr Phe Leu Thr Ala Gln Thr Phe Leu Met Asp Leu
    290                 295                 300

Gly Gln Phe Leu Leu Phe Cys His Ile Ser Ser His His His Gly Gly
305                 310                 315                 320

Met Glu Ala His Val Arg Val Glu Ser Cys Ala Glu Glu Pro Gln Leu
                325                 330                 335

Arg Arg Lys Ala Asp Glu Glu Glu Asp Tyr Asp Asp Asn Leu Tyr Asp
            340                 345                 350

Ser Asp Met Asp Val Val Arg Leu Asp Gly Asp Asp Val Ser Pro Phe
        355                 360                 365

Ile Gln Ile Arg Ser Val Ala Lys Lys His Pro Lys Thr Trp Val His
    370                 375                 380

Tyr Ile Ser Ala Glu Glu Glu Asp Trp Asp Tyr Ala Pro Ala Val Pro
385                 390                 395                 400

Ser Pro Ser Asp Arg Ser Tyr Lys Ser Leu Tyr Leu Asn Ser Gly Pro
                405                 410                 415

Gln Arg Ile Gly Arg Lys Tyr Lys Lys Ala Arg Phe Val Ala Tyr Thr
            420                 425                 430

Asp Val Thr Phe Lys Thr Arg Lys Ala Ile Pro Tyr Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Lys Ala Ser Arg Pro Tyr Asn Ile Tyr Pro His Gly Ile
465                 470                 475                 480

Thr Asp Val Ser Ala Leu His Pro Gly Arg Leu Leu Lys Gly Trp Lys
                485                 490                 495

His Leu Lys Asp Met Pro Ile Leu Pro Gly Glu Thr Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Ser Ile Asn Leu Glu Lys Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Met Met Ser Asp Lys Arg Asn Val Ile Leu Phe
                565                 570                 575

Ser Val Phe Asp Glu Asn Gln Ser Trp Tyr Leu Ala Glu Asn Ile Gln
            580                 585                 590

Arg Phe Leu Pro Asn Pro Asp Gly Leu Gln Pro Gln Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Val Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
```

```
            660                 665                 670

Phe Ser Gly Glu Thr Val Phe Met Ser Met Glu Asn Pro Gly Leu Trp
        675                 680                 685

Val Leu Gly Cys His Asn Ser Asp Leu Arg Asn Arg Gly Met Thr Ala
    690                 695                 700

Leu Leu Lys Val Tyr Ser Cys Asp Arg Asp Ile Gly Asp Tyr Tyr Asp
705                 710                 715                 720

Asn Thr Tyr Glu Asp Ile Pro Gly Phe Leu Leu Ser Gly Lys Asn Val
                725                 730                 735

Ile Glu Pro Arg Ser Phe Ser Gln Asn Pro Pro Val Leu Lys Arg His
            740                 745                 750

Gln Arg Asp Ile Ser Leu Pro Thr Phe Gln Pro Glu Glu Asp Lys Met
        755                 760                 765

Asp Tyr Asp Asp Ile Phe Ser Thr Glu Thr Lys Gly Glu Asp Phe Asp
    770                 775                 780

Ile Tyr Gly Glu Asp Glu Asn Gln Asp Pro Arg Ser Phe Gln Lys Arg
785                 790                 795                 800

Thr Arg His Tyr Phe Ile Ala Ala Val Glu Gln Leu Trp Asp Tyr Gly
                805                 810                 815

Met Ser Glu Ser Pro Arg Ala Leu Arg Asn Arg Ala Gln Asn Gly Glu
            820                 825                 830

Val Pro Arg Phe Lys Lys Val Val Phe Arg Glu Phe Ala Asp Gly Ser
        835                 840                 845

Phe Thr Gln Pro Ser Tyr Arg Gly Glu Leu Asn Lys His Leu Gly Leu
    850                 855                 860

Leu Gly Pro Tyr Ile Arg Ala Glu Val Glu Asp Asn Ile Met Val Thr
865                 870                 875                 880

Phe Lys Asn Gln Ala Ser Arg Pro Tyr Ser Phe Tyr Ser Ser Leu Ile
                885                 890                 895

Ser Tyr Pro Asp Asp Gln Glu Gln Gly Ala Glu Pro Arg His Asn Phe
            900                 905                 910

Val Gln Pro Asn Glu Thr Arg Thr Tyr Phe Trp Lys Val Gln His His
        915                 920                 925

Met Ala Pro Thr Glu Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Ile Cys Arg Ala Asn Thr Leu Asn Ala Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn  Val Glu Arg Asn Cys  Arg Ala Pro
        995                 1000                 1005

Cys His  Leu Gln Met Glu Asp  Pro Thr Leu Lys Glu  Asn Tyr Arg
    1010                 1015                 1020

Phe His  Ala Ile Asn Gly Tyr  Val Met Asp Thr Leu  Pro Gly Leu
    1025                 1030                 1035

Val Met  Ala Gln Asn Gln Arg  Ile Arg Trp Tyr Leu  Leu Ser Met
    1040                 1045                 1050

Gly Ser  Asn Glu Asn Ile His  Ser Ile His Phe Ser  Gly His Val
    1055                 1060                 1065

Phe Ser  Val Arg Lys Lys Glu  Glu Tyr Lys Met Ala  Val Tyr Asn
    1070                 1075                 1080
```

```
Leu Tyr  Pro Gly Val Phe Glu  Thr Val Glu Met Leu  Pro Ser Lys
    1085                 1090                 1095

Val Gly  Ile Trp Arg Ile Glu  Cys Leu Ile Gly Glu  His Leu Gln
    1100                 1105                 1110

Ala Gly  Met Ser Thr Thr Phe  Leu Val Tyr Ser Lys  Glu Cys Gln
    1115                 1120                 1125

Ala Pro  Leu Gly Met Ala Ser  Gly Arg Ile Arg Asp  Phe Gln Ile
    1130                 1135                 1140

Thr Ala  Ser Gly Gln Tyr Gly  Gln Trp Ala Pro Lys  Leu Ala Arg
    1145                 1150                 1155

Leu His  Tyr Ser Gly Ser Ile  Asn Ala Trp Ser Thr  Lys Asp Pro
    1160                 1165                 1170

His Ser  Trp Ile Lys Val Asp  Leu Leu Ala Pro Met  Ile Ile His
    1175                 1180                 1185

Gly Ile  Met Thr Gln Gly Ala  Arg Gln Lys Phe Ser  Ser Leu Tyr
    1190                 1195                 1200

Ile Ser  Gln Phe Ile Ile Met  Tyr Ser Leu Asp Gly  Arg Asn Trp
    1205                 1210                 1215

Gln Ser  Tyr Arg Gly Asn Ser  Thr Gly Thr Leu Met  Val Phe Phe
    1220                 1225                 1230

Gly Asn  Val Asp Ala Ser Gly  Ile Lys His Asn Ile  Phe Asn Pro
    1235                 1240                 1245

Pro Ile  Val Ala Arg Tyr Ile  Arg Leu His Pro Thr  His Tyr Ser
    1250                 1255                 1260

Ile Arg  Ser Thr Leu Arg Met  Glu Leu Met Gly Cys  Asp Leu Asn
    1265                 1270                 1275

Ser Cys  Ser Met Pro Leu Gly  Met Gln Asn Lys Ala  Ile Ser Asp
    1280                 1285                 1290

Ser Gln  Ile Thr Ala Ser Ser  His Leu Ser Asn Ile  Phe Ala Thr
    1295                 1300                 1305

Trp Ser  Pro Ser Gln Ala Arg  Leu His Leu Gln Gly  Arg Thr Asn
    1310                 1315                 1320

Ala Trp  Arg Pro Arg Val Ser  Ser Ala Glu Glu Trp  Leu Gln Val
    1325                 1330                 1335

Asp Leu  Gln Lys Thr Val Lys  Val Thr Gly Ile Thr  Thr Gln Gly
    1340                 1345                 1350

Val Lys  Ser Leu Leu Ser Ser  Met Tyr Val Lys Glu  Phe Leu Val
    1355                 1360                 1365

Ser Ser  Ser Gln Asp Gly Arg  Arg Trp Thr Leu Phe  Leu Gln Asp
    1370                 1375                 1380

Gly His  Thr Lys Val Phe Gln  Gly Asn Gln Asp Ser  Ser Thr Pro
    1385                 1390                 1395

Val Val  Asn Ala Leu Asp Pro  Pro Leu Phe Thr Arg  Tyr Leu Arg
    1400                 1405                 1410

Ile His  Pro Thr Ser Trp Ala  Gln His Ile Ala Leu  Arg Leu Glu
    1415                 1420                 1425

Leu Leu  Gly Cys Glu Ala Gln  Gln His Val
    1430                 1435
```

<210> SEQ ID NO 9
<211> LENGTH: 1438
<212> TYPE: PRT
<213> ORGANISM: Porcine

-continued

<400> SEQUENCE: 9

```
Ala Ile Arg Arg Tyr Tyr Leu Gly Ala Val Glu Leu Ser Trp Asp Tyr
1               5                   10                  15

Arg Gln Ser Glu Leu Leu Arg Glu Leu His Val Asp Thr Arg Phe Pro
            20                  25                  30

Ala Thr Ala Pro Gly Ala Leu Pro Leu Gly Pro Ser Val Leu Tyr Lys
        35                  40                  45

Lys Thr Val Phe Val Glu Phe Thr Asp Gln Leu Phe Ser Val Ala Arg
    50                  55                  60

Pro Arg Pro Pro Trp Met Gly Leu Leu Gly Pro Thr Ile Gln Ala Glu
65                  70                  75                  80

Val Tyr Asp Thr Val Val Val Thr Leu Lys Asn Met Ala Ser His Pro
                85                  90                  95

Val Ser Leu His Ala Val Gly Val Ser Phe Trp Lys Ser Ser Glu Gly
            100                 105                 110

Ala Glu Tyr Glu Asp His Thr Ser Gln Arg Glu Lys Glu Asp Asp Lys
        115                 120                 125

Val Leu Pro Gly Lys Ser Gln Thr Tyr Val Trp Gln Val Leu Lys Glu
    130                 135                 140

Asn Gly Pro Thr Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Arg Glu Gly Ser Leu Thr Arg Glu Arg Thr Gln Asn
            180                 185                 190

Leu His Glu Phe Val Leu Leu Phe Ala Val Phe Asp Glu Gly Lys Ser
        195                 200                 205

Trp His Ser Ala Arg Asn Asp Ser Trp Thr Arg Ala Met Asp Pro Ala
    210                 215                 220

Pro Ala Arg Ala Gln Pro Ala Met His Thr Val Asn Gly Tyr Val Asn
225                 230                 235                 240

Arg Ser Leu Pro Gly Leu Ile Gly Cys His Lys Lys Ser Val Tyr Trp
                245                 250                 255

His Val Ile Gly Met Gly Thr Ser Pro Glu Val His Ser Ile Phe Leu
            260                 265                 270

Glu Gly His Thr Phe Leu Val Arg His His Arg Gln Ala Ser Leu Glu
        275                 280                 285

Ile Ser Pro Leu Thr Phe Leu Thr Ala Gln Thr Phe Leu Met Asp Leu
    290                 295                 300

Gly Gln Phe Leu Leu Phe Cys His Ile Ser Ser His His His Gly Gly
305                 310                 315                 320

Met Glu Ala His Val Arg Val Glu Ser Cys Ala Glu Glu Pro Gln Leu
                325                 330                 335

Arg Arg Lys Ala Asp Glu Glu Glu Asp Tyr Asp Asp Asn Leu Tyr Asp
            340                 345                 350

Ser Asp Met Asp Val Val Arg Leu Asp Gly Asp Asp Val Ser Pro Phe
        355                 360                 365

Ile Gln Ile Arg Ser Val Ala Lys Lys His Pro Lys Thr Trp Val His
    370                 375                 380

Tyr Ile Ser Ala Glu Glu Glu Asp Trp Asp Tyr Ala Pro Ala Val Pro
385                 390                 395                 400

Ser Pro Ser Asp Arg Ser Tyr Lys Ser Leu Tyr Leu Asn Ser Gly Pro
                405                 410                 415
```

-continued

```
Gln Arg Ile Gly Arg Lys Tyr Lys Lys Ala Arg Phe Val Ala Tyr Thr
            420                 425                 430

Asp Val Thr Phe Lys Thr Arg Lys Ala Ile Pro Tyr Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Lys Ala Ser Arg Pro Tyr Asn Ile Tyr Pro His Gly Ile
465                 470                 475                 480

Thr Asp Val Ser Ala Leu His Pro Gly Arg Leu Leu Lys Gly Trp Lys
                485                 490                 495

His Leu Lys Asp Met Pro Ile Leu Pro Gly Glu Thr Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Ser Ile Asn Leu Glu Lys Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Met Met Ser Asp Lys Arg Asn Val Ile Leu Phe
                565                 570                 575

Ser Val Phe Asp Glu Asn Gln Ser Trp Tyr Leu Ala Glu Asn Ile Gln
            580                 585                 590

Arg Phe Leu Pro Asn Pro Asp Gly Leu Gln Pro Gln Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Val Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Val Leu Gly Cys His Asn Ser Asp Leu Arg Asn Arg Gly Met Thr Ala
    690                 695                 700

Leu Leu Lys Val Tyr Ser Cys Asp Arg Asp Ile Gly Asp Tyr Tyr Asp
705                 710                 715                 720

Asn Thr Tyr Glu Asp Ile Pro Gly Phe Leu Leu Ser Gly Lys Asn Val
                725                 730                 735

Ile Glu Pro Arg Ser Phe Ser Gln Asn Pro Pro Val Leu Lys Arg His
            740                 745                 750

Gln Arg Asp Ile Ser Leu Pro Thr Phe Gln Pro Glu Glu Asp Lys Met
        755                 760                 765

Asp Tyr Asp Asp Ile Phe Ser Thr Glu Thr Lys Gly Glu Asp Phe Asp
    770                 775                 780

Ile Tyr Gly Glu Asp Glu Asn Gln Asp Pro Arg Ser Phe Gln Lys Arg
785                 790                 795                 800

Thr Arg His Tyr Phe Ile Ala Ala Val Glu Gln Leu Trp Asp Tyr Gly
                805                 810                 815

Met Ser Glu Ser Pro Arg Ala Leu Arg Asn Arg Ala Gln Asn Gly Glu
            820                 825                 830
```

```
Val Pro Arg Phe Lys Lys Val Val Phe Arg Glu Phe Ala Asp Gly Ser
        835                 840                 845

Phe Thr Gln Pro Ser Tyr Arg Gly Glu Leu Asn Lys His Leu Gly Leu
    850                 855                 860

Leu Gly Pro Tyr Ile Arg Ala Glu Val Glu Asp Asn Ile Met Val Thr
865                 870                 875                 880

Phe Lys Asn Gln Ala Ser Arg Pro Tyr Ser Phe Tyr Ser Ser Leu Ile
                885                 890                 895

Ser Tyr Pro Asp Asp Gln Glu Gln Gly Ala Glu Pro Arg His Asn Phe
            900                 905                 910

Val Gln Pro Asn Glu Thr Arg Thr Tyr Phe Trp Lys Val Gln His His
        915                 920                 925

Met Ala Pro Thr Glu Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Ile Cys Arg Ala Asn Thr Leu Asn Ala Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn  Val Glu Arg Asn Cys  Arg Ala Pro
        995                 1000                1005

Cys His  Leu Gln Met Glu Asp  Pro Thr Leu Lys Glu  Asn Tyr Arg
    1010                1015                1020

Phe His  Ala Ile Asn Gly Tyr  Val Met Asp Thr Leu  Pro Gly Leu
    1025                1030                1035

Val Met  Ala Gln Asn Gln Arg  Ile Arg Trp Tyr Leu  Leu Ser Met
    1040                1045                1050

Gly Ser  Asn Glu Asn Ile His  Ser Ile His Phe Ser  Gly His Val
    1055                1060                1065

Phe Ser  Val Arg Lys Lys Glu  Glu Tyr Lys Met Ala  Val Tyr Asn
    1070                1075                1080

Leu Tyr  Pro Gly Val Phe Glu  Thr Val Glu Met Leu  Pro Ser Lys
    1085                1090                1095

Val Gly  Ile Trp Arg Ile Glu  Cys Leu Ile Gly Glu  His Leu Gln
    1100                1105                1110

Ala Gly  Met Ser Thr Thr Phe  Leu Val Tyr Ser Lys  Glu Cys Gln
    1115                1120                1125

Ala Pro  Leu Gly Met Ala Ser  Gly Arg Ile Arg Asp  Phe Gln Ile
    1130                1135                1140

Thr Ala  Ser Gly Gln Tyr Gly  Gln Trp Ala Pro Lys  Leu Ala Arg
    1145                1150                1155

Leu His  Tyr Ser Gly Ser Ile  Asn Ala Trp Ser Thr  Lys Asp Pro
    1160                1165                1170

His Ser  Trp Ile Lys Val Asp  Leu Leu Ala Pro Met  Ile Ile His
    1175                1180                1185

Gly Ile  Met Thr Gln Gly Ala  Arg Gln Lys Phe Ser  Ser Leu Tyr
    1190                1195                1200

Ile Ser  Gln Phe Ile Ile Met  Tyr Ser Leu Asp Gly  Arg Asn Trp
    1205                1210                1215

Gln Ser  Tyr Arg Gly Asn Ser  Thr Gly Thr Leu Met  Val Phe Phe
    1220                1225                1230

Gly Asn  Val Asp Ala Ser Gly  Ile Lys His Asn Ile  Phe Asn Pro
```

```
    1235                1240                1245

Pro Ile  Val Ala Arg Tyr Ile  Arg Leu His Pro Thr  His Tyr Ser
    1250                1255                1260

Ile Arg  Ser Thr Leu Arg Met  Glu Leu Met Gly Cys  Asp Leu Asn
    1265                1270                1275

Ser Cys  Ser Met Pro Leu Gly  Met Gln Asn Lys Ala  Ile Ser Asp
    1280                1285                1290

Ser Gln  Ile Thr Ala Ser Ser  His Leu Ser Asn Ile  Phe Ala Thr
    1295                1300                1305

Trp Ser  Pro Ser Gln Ala Arg  Leu His Leu Gln Gly  Arg Thr Asn
    1310                1315                1320

Ala Trp  Arg Pro Arg Val Ser  Ser Ala Glu Glu Trp  Leu Gln Val
    1325                1330                1335

Asp Leu  Gln Lys Thr Val Lys  Val Thr Gly Ile Thr  Thr Gln Gly
    1340                1345                1350

Val Lys  Ser Leu Leu Ser Ser  Met Tyr Val Lys Glu  Phe Leu Val
    1355                1360                1365

Ser Ser  Ser Gln Asp Gly Arg  Arg Trp Thr Leu Phe  Leu Gln Asp
    1370                1375                1380

Gly His  Thr Lys Val Phe Gln  Gly Asn Gln Asp Ser  Ser Thr Pro
    1385                1390                1395

Val Val  Asn Ala Leu Asp Pro  Pro Leu Phe Thr Arg  Tyr Leu Arg
    1400                1405                1410

Ile His  Pro Thr Ser Trp Ala  Gln His Ile Ala Leu  Arg Leu Glu
    1415                1420                1425

Val Leu  Gly Cys Glu Ala Gln  Asp Leu Tyr
    1430                1435


<210> SEQ ID NO 10
<211> LENGTH: 1432
<212> TYPE: PRT
<213> ORGANISM: Canine

<400> SEQUENCE: 10

Ala Thr Arg Lys Tyr Tyr Leu Gly Ala Val Glu Leu Ser Trp Asp Tyr
1               5                   10                  15

Met Gln Ser Asp Leu Leu Ser Ala Leu His Ala Asp Thr Ser Phe Ser
            20                  25                  30

Ser Arg Val Pro Gly Ser Leu Pro Leu Thr Thr Ser Val Thr Tyr Arg
        35                  40                  45

Lys Thr Val Phe Val Glu Phe Thr Asp Asp Leu Phe Asn Ile Ala Lys
    50                  55                  60

Pro Arg Pro Pro Trp Met Gly Leu Leu Gly Pro Thr Ile Gln Ala Glu
65                  70                  75                  80

Val Tyr Asp Thr Val Val Ile Val Leu Lys Asn Met Ala Ser His Pro
                85                  90                  95

Val Ser Leu His Ala Val Gly Val Ser Tyr Trp Lys Ala Ser Glu Gly
            100                 105                 110

Ala Glu Tyr Glu Asp Gln Thr Ser Gln Lys Glu Lys Glu Asp Asp Asn
        115                 120                 125

Val Ile Pro Gly Glu Ser His Thr Tyr Val Trp Gln Val Leu Lys Glu
    130                 135                 140

Asn Gly Pro Met Ala Ser Asp Pro Pro Cys Leu Thr Tyr Ser Tyr Phe
145                 150                 155                 160
```

-continued

```
Ser His Val Asp Leu Val Lys Asp Leu Asn Ser Gly Leu Ile Gly Ala
                165                 170                 175

Leu Leu Val Cys Lys Glu Gly Ser Leu Ala Lys Glu Arg Thr Gln Thr
            180                 185                 190

Leu Gln Glu Phe Val Leu Leu Phe Ala Val Phe Asp Glu Gly Lys Ser
        195                 200                 205

Trp His Ser Glu Thr Asn Ala Ser Leu Thr Gln Ala Glu Ala Gln His
    210                 215                 220

Glu Leu His Thr Ile Asn Gly Tyr Val Asn Arg Ser Leu Pro Gly Leu
225                 230                 235                 240

Thr Val Cys His Lys Arg Ser Val Tyr Trp His Val Ile Gly Met Gly
                245                 250                 255

Thr Thr Pro Glu Val His Ser Ile Phe Leu Glu Gly His Thr Phe Leu
            260                 265                 270

Val Gly Asn His Arg Gln Ala Ser Leu Glu Ile Ser Pro Ile Thr Phe
        275                 280                 285

Leu Thr Ala Gln Thr Phe Leu Met Asp Leu Gly Gln Phe Leu Leu Phe
    290                 295                 300

Cys His Ile Pro Ser His Gln His Asp Gly Met Glu Ala Tyr Val Lys
305                 310                 315                 320

Val Asp Ser Cys Pro Glu Glu Pro Gln Leu Arg Met Lys Asn Asn Glu
                325                 330                 335

Asp Lys Asp Tyr Asp Asp Gly Leu Tyr Gly Ser Asp Met Asp Val Val
            340                 345                 350

Ser Phe Asp Asp Asp Ser Ser Ser Pro Phe Ile Gln Ile Arg Ser Val
        355                 360                 365

Ala Lys Lys His Pro Lys Thr Trp Val His Tyr Ile Ala Ala Glu Glu
    370                 375                 380

Glu Asp Trp Asp Tyr Ala Pro Ser Gly Pro Thr Pro Asn Asp Arg Ser
385                 390                 395                 400

His Lys Asn Leu Tyr Leu Asn Asn Gly Pro Gln Arg Ile Gly Lys Lys
                405                 410                 415

Tyr Lys Lys Val Arg Phe Val Ala Tyr Thr Asp Glu Thr Phe Lys Thr
            420                 425                 430

Arg Glu Ala Ile Gln Tyr Glu Ser Gly Ile Leu Gly Pro Leu Leu Tyr
        435                 440                 445

Gly Glu Val Gly Asp Thr Leu Leu Ile Ile Phe Lys Lys Gln Ala Ser
    450                 455                 460

Arg Pro Tyr Asn Ile Tyr Pro His Gly Ile Asn Tyr Val Thr Pro Leu
465                 470                 475                 480

His Thr Gly Arg Leu Pro Lys Gly Val Lys His Leu Lys Asp Met Pro
                485                 490                 495

Ile Leu Pro Gly Glu Ile Phe Lys Tyr Lys Trp Thr Val Thr Val Glu
            500                 505                 510

Asp Gly Pro Thr Lys Ser Asp Pro Arg Cys Leu Thr Arg Tyr Tyr Ser
        515                 520                 525

Ser Phe Ile Asn Leu Glu Arg Asp Leu Ala Ser Gly Leu Ile Gly Pro
    530                 535                 540

Leu Leu Ile Cys Tyr Lys Glu Ser Val Asp Gln Arg Gly Asn Gln Met
545                 550                 555                 560

Met Ser Asp Lys Arg Asn Val Ile Leu Phe Ser Val Leu Asp Glu Asn
                565                 570                 575

Arg Ser Trp Tyr Leu Thr Glu Asp Met Gln Arg Phe Leu Pro Asn Ala
```

580 585 590

Asp Val Val Gln Pro His Asp Pro Glu Phe Gln Leu Ser Asn Ile Met
595 600 605

His Ser Ile Asn Gly Tyr Val Phe Asp Asn Leu Gln Leu Ser Val Cys
610 615 620

Leu His Glu Val Ala Tyr Trp Tyr Ile Leu Ser Val Gly Ala Gln Thr
625 630 635 640

Asp Phe Leu Ser Val Phe Phe Ser Gly Tyr Thr Phe Lys His Lys Met
645 650 655

Val Tyr Glu Asp Thr Leu Thr Leu Phe Pro Phe Ser Gly Glu Thr Val
660 665 670

Phe Met Ser Met Glu Asn Pro Gly Leu Trp Val Leu Gly Cys His Asn
675 680 685

Ser Asp Phe Arg Asn Arg Gly Met Thr Ala Leu Leu Lys Val Ser Ser
690 695 700

Cys Asn Arg Asn Ile Asp Asp Tyr Tyr Glu Asp Thr Tyr Glu Asp Ile
705 710 715 720

Pro Thr Pro Leu Leu Asn Glu Asn Asn Val Ile Lys Pro Arg Ser Phe
725 730 735

Ser Gln Asn Pro Pro Val Leu Lys Arg His Gln Arg Glu Ile Thr Val
740 745 750

Thr Thr Leu Gln Pro Glu Glu Asp Lys Phe Glu Tyr Asp Asp Thr Phe
755 760 765

Ser Ile Glu Met Lys Arg Glu Asp Phe Asp Ile Tyr Gly Asp Tyr Glu
770 775 780

Asp Gln Gly Leu Arg Ser Phe Gln Lys Lys Thr Arg His Tyr Phe Ile
785 790 795 800

Ala Ala Val Glu Arg Leu Trp Asp Tyr Gly Met Ser Arg Ser Pro His
805 810 815

Ile Leu Arg Asn Arg Ala Gln Ser Gly Asp Val Gln Gln Phe Lys Lys
820 825 830

Val Val Phe Gln Glu Phe Thr Asp Gly Ser Phe Thr Gln Pro Leu Tyr
835 840 845

Arg Gly Glu Leu Asn Glu His Leu Gly Leu Leu Gly Pro Tyr Ile Arg
850 855 860

Ala Glu Val Glu Asp Asn Ile Val Val Thr Phe Lys Asn Gln Ala Ser
865 870 875 880

Arg Pro Tyr Ser Phe Tyr Ser Ser Leu Ile Ser Tyr Asp Glu Asp Glu
885 890 895

Gly Gln Gly Ala Glu Pro Arg Arg Lys Phe Val Asn Pro Asn Glu Thr
900 905 910

Lys Ile Tyr Phe Trp Lys Val Gln His His Met Ala Pro Thr Lys Asp
915 920 925

Glu Phe Asp Cys Lys Ala Trp Ala Tyr Phe Ser Asp Val Asp Leu Glu
930 935 940

Lys Asp Val His Ser Gly Leu Ile Gly Pro Leu Leu Ile Cys Arg Ser
945 950 955 960

Asn Thr Leu Asn Pro Ala His Gly Arg Gln Val Thr Val Gln Glu Phe
965 970 975

Ala Leu Val Phe Thr Ile Phe Asp Glu Thr Lys Ser Trp Tyr Phe Thr
980 985 990

Glu Asn Leu Glu Arg Asn Cys Arg Ala Pro Cys Asn Val Gln Lys Glu
995 1000 1005

-continued

```
Asp Pro  Thr Leu Lys Glu Asn  Phe Arg Phe His Ala  Ile Asn Gly
    1010                 1015                 1020

Tyr Val  Lys Asp Thr Leu Pro  Gly Leu Val Met Ala  Gln Asp Gln
    1025                 1030                 1035

Lys Val  Arg Trp Tyr Leu Leu  Ser Met Gly Ser Asn  Glu Asn Ile
    1040                 1045                 1050

His Ser  Ile His Phe Ser Gly  His Val Phe Thr Val  Arg Lys Lys
    1055                 1060                 1065

Glu Glu  Tyr Lys Met Ala Val  Tyr Asn Leu Tyr Pro  Gly Val Phe
    1070                 1075                 1080

Glu Thr  Val Glu Met Leu Pro  Ser Gln Val Gly Ile  Trp Arg Ile
    1085                 1090                 1095

Glu Cys  Leu Ile Gly Glu His  Leu Gln Ala Gly Met  Ser Thr Leu
    1100                 1105                 1110

Phe Leu  Val Tyr Ser Lys Lys  Cys Gln Thr Pro Leu  Gly Met Ala
    1115                 1120                 1125

Ser Gly  His Ile Arg Asp Phe  Gln Ile Thr Ala Ser  Gly Gln Tyr
    1130                 1135                 1140

Gly Gln  Trp Ala Pro Lys Leu  Ala Arg Leu His Tyr  Ser Gly Ser
    1145                 1150                 1155

Ile Asn  Ala Trp Ser Thr Lys  Asp Pro Phe Ser Trp  Ile Lys Val
    1160                 1165                 1170

Asp Leu  Leu Ala Pro Met Ile  Ile His Gly Ile Met  Thr Gln Gly
    1175                 1180                 1185

Ala Arg  Gln Lys Phe Ser Ser  Leu Tyr Val Ser Gln  Phe Ile Ile
    1190                 1195                 1200

Met Tyr  Ser Leu Asp Gly Asn  Lys Trp His Ser Tyr  Arg Gly Asn
    1205                 1210                 1215

Ser Thr  Gly Thr Leu Met Val  Phe Phe Gly Asn Val  Asp Ser Ser
    1220                 1225                 1230

Gly Ile  Lys His Asn Ile Phe  Asn Pro Pro Ile Ile  Ala Gln Tyr
    1235                 1240                 1245

Ile Arg  Leu His Pro Thr His  Tyr Ser Ile Arg Ser  Thr Leu Arg
    1250                 1255                 1260

Met Glu  Leu Leu Gly Cys Asp  Phe Asn Ser Cys Ser  Met Pro Leu
    1265                 1270                 1275

Gly Met  Glu Ser Lys Ala Ile  Ser Asp Ala Gln Ile  Thr Ala Ser
    1280                 1285                 1290

Ser Tyr  Leu Ser Ser Met Leu  Ala Thr Trp Ser Pro  Ser Gln Ala
    1295                 1300                 1305

Arg Leu  His Leu Gln Gly Arg  Thr Asn Ala Trp Arg  Pro Gln Ala
    1310                 1315                 1320

Asn Asn  Pro Lys Glu Trp Leu  Gln Val Asp Phe Arg  Lys Thr Met
    1325                 1330                 1335

Lys Val  Thr Gly Ile Thr Thr  Gln Gly Val Lys Ser  Leu Leu Ile
    1340                 1345                 1350

Ser Met  Tyr Val Lys Glu Phe  Leu Ile Ser Ser Ser  Gln Asp Gly
    1355                 1360                 1365

His Asn  Trp Thr Leu Phe Leu  Gln Asn Asp Lys Val  Lys Val Phe
    1370                 1375                 1380

Gln Gly  Asn Arg Asp Ser Ser  Thr Pro Val Arg Asn  Ala Leu Glu
    1385                 1390                 1395
```

-continued

Pro Pro Leu Val Ala Arg Tyr Val Arg Leu His Pro Gln Ser Trp
1400 1405 1410

Ala His His Ile Ala Leu Arg Leu Glu Val Leu Gly Cys Asp Thr
1415 1420 1425

Gln Gln Pro Ala
1430

<210> SEQ ID NO 11
<211> LENGTH: 19
<212> TYPE: PRT
<213> ORGANISM: Homo sapiens

<400> SEQUENCE: 11

Met Gln Ile Glu Leu Ser Thr Cys Phe Phe Leu Cys Leu Leu Arg Phe
1 5 10 15

Cys Phe Ser

<210> SEQ ID NO 12
<211> LENGTH: 19
<212> TYPE: PRT
<213> ORGANISM: Porcine

<400> SEQUENCE: 12

Met Gln Leu Glu Leu Ser Thr Cys Val Phe Leu Cys Leu Leu Pro Leu
1 5 10 15

Gly Phe Ser

<210> SEQ ID NO 13
<211> LENGTH: 19
<212> TYPE: PRT
<213> ORGANISM: Canine

<400> SEQUENCE: 13

Met Gln Val Glu Leu Tyr Thr Cys Cys Phe Leu Cys Leu Leu Pro Phe
1 5 10 15

Ser Leu Ser

<210> SEQ ID NO 14
<211> LENGTH: 22
<212> TYPE: PRT
<213> ORGANISM: Homo sapiens

<400> SEQUENCE: 14

Met Ile Pro Ala Arg Phe Ala Gly Val Leu Leu Ala Leu Ala Leu Ile
1 5 10 15

Leu Pro Gly Thr Leu Cys
20

<210> SEQ ID NO 15
<211> LENGTH: 711
<212> TYPE: PRT
<213> ORGANISM: Homo sapiens

<400> SEQUENCE: 15

Ser Leu Ser Cys Arg Pro Pro Met Val Lys Leu Val Cys Pro Ala Asp
1 5 10 15

Asn Leu Arg Ala Glu Gly Leu Glu Cys Thr Lys Thr Cys Gln Asn Tyr
20 25 30

Asp Leu Glu Cys Met Ser Met Gly Cys Val Ser Gly Cys Leu Cys Pro
35 40 45

-continued

```
Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Ala
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Ala Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
```

-continued

```
465                 470                 475                 480

Val Val Pro Pro Asp Lys Thr His Thr Cys Pro Pro Cys Pro Ala Pro
                485                 490                 495

Glu Leu Leu Gly Gly Pro Ser Val Phe Leu Phe Pro Pro Lys Pro Lys
            500                 505                 510

Asp Thr Leu Met Ile Ser Arg Thr Pro Glu Val Thr Cys Val Val Val
        515                 520                 525

Asp Val Ser His Glu Asp Pro Glu Val Lys Phe Asn Trp Tyr Val Asp
    530                 535                 540

Gly Val Glu Val His Asn Ala Lys Thr Lys Pro Arg Glu Glu Gln Tyr
545                 550                 555                 560

Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
            580                 585                 590

Pro Ala Pro Ile Glu Lys Thr Ile Ser Lys Ala Lys Gly Gln Pro Arg
        595                 600                 605

Glu Pro Gln Val Tyr Thr Leu Pro Pro Ser Arg Asp Glu Leu Thr Lys
    610                 615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
            660                 665                 670

Lys Leu Thr Val Asp Lys Ser Arg Trp Gln Gln Gly Asn Val Phe Ser
        675                 680                 685

Cys Ser Val Met His Glu Ala Leu His Asn His Tyr Thr Gln Lys Ser
    690                 695                 700

Leu Ser Leu Ser Pro Gly Lys
705                 710


<210> SEQ ID NO 16
<211> LENGTH: 1452
<212> TYPE: PRT
<213> ORGANISM: Homo sapiens

<400> SEQUENCE: 16

Ala Glu Gly Thr Arg Gly Arg Ser Ser Thr Ala Arg Cys Ser Leu Phe
1               5                   10                  15

Gly Ser Asp Phe Val Asn Thr Phe Asp Gly Ser Met Tyr Ser Phe Ala
            20                  25                  30

Gly Tyr Cys Ser Tyr Leu Leu Ala Gly Gly Cys Gln Lys Arg Ser Phe
        35                  40                  45

Ser Ile Ile Gly Asp Phe Gln Asn Gly Lys Arg Val Ser Leu Ser Val
    50                  55                  60

Tyr Leu Gly Glu Phe Phe Asp Ile His Leu Phe Val Asn Gly Thr Val
65                  70                  75                  80

Thr Gln Gly Asp Gln Arg Val Ser Met Pro Tyr Ala Ser Lys Gly Leu
                85                  90                  95

Tyr Leu Glu Thr Glu Ala Gly Tyr Tyr Lys Leu Ser Gly Glu Ala Tyr
            100                 105                 110

Gly Phe Val Ala Arg Ile Asp Gly Ser Gly Asn Phe Gln Val Leu Leu
        115                 120                 125
```

-continued

```
Ser Asp Arg Tyr Phe Asn Lys Thr Cys Gly Leu Cys Gly Asn Phe Asn
    130                 135                 140

Ile Phe Ala Glu Asp Asp Phe Met Thr Gln Glu Gly Thr Leu Thr Ser
145                 150                 155                 160

Asp Pro Tyr Asp Phe Ala Asn Ser Trp Ala Leu Ser Ser Gly Glu Gln
                165                 170                 175

Trp Cys Glu Arg Ala Ser Pro Pro Ser Ser Ser Cys Asn Ile Ser Ser
            180                 185                 190

Gly Glu Met Gln Lys Gly Leu Trp Glu Gln Cys Gln Leu Leu Lys Ser
        195                 200                 205

Thr Ser Val Phe Ala Arg Cys His Pro Leu Val Asp Pro Glu Pro Phe
    210                 215                 220

Val Ala Leu Cys Glu Lys Thr Leu Cys Glu Cys Ala Gly Gly Leu Glu
225                 230                 235                 240

Cys Ala Cys Pro Ala Leu Leu Glu Tyr Ala Arg Thr Cys Ala Gln Glu
                245                 250                 255

Gly Met Val Leu Tyr Gly Trp Thr Asp His Ser Ala Cys Ser Pro Val
            260                 265                 270

Cys Pro Ala Gly Met Glu Tyr Arg Gln Cys Val Ser Pro Cys Ala Arg
        275                 280                 285

Thr Cys Gln Ser Leu His Ile Asn Glu Met Cys Gln Glu Arg Cys Val
    290                 295                 300

Asp Gly Cys Ser Cys Pro Glu Gly Gln Leu Leu Asp Glu Gly Leu Cys
305                 310                 315                 320

Val Glu Ser Thr Glu Cys Pro Cys Val His Ser Gly Lys Arg Tyr Pro
                325                 330                 335

Pro Gly Thr Ser Leu Ser Arg Asp Cys Asn Thr Cys Ile Cys Arg Asn
            340                 345                 350

Ser Gln Trp Ile Cys Ser Asn Glu Glu Cys Pro Gly Glu Cys Leu Val
        355                 360                 365

Thr Gly Gln Ser His Phe Lys Ser Phe Asp Asn Arg Tyr Phe Thr Phe
    370                 375                 380

Ser Gly Ile Cys Gln Tyr Leu Leu Ala Arg Asp Cys Gln Asp His Ser
385                 390                 395                 400

Phe Ser Ile Val Ile Glu Thr Val Gln Cys Ala Asp Asp Arg Asp Ala
                405                 410                 415

Val Cys Thr Arg Ser Val Thr Val Arg Leu Pro Gly Leu His Asn Ser
            420                 425                 430

Leu Val Lys Leu Lys His Gly Ala Gly Val Ala Met Asp Gly Gln Asp
        435                 440                 445

Ile Gln Leu Pro Leu Leu Lys Gly Asp Leu Arg Ile Gln His Thr Val
    450                 455                 460

Thr Ala Ser Val Arg Leu Ser Tyr Gly Glu Asp Leu Gln Met Asp Trp
465                 470                 475                 480

Asp Gly Arg Gly Arg Leu Leu Val Lys Leu Ser Pro Val Tyr Ala Gly
                485                 490                 495

Lys Thr Cys Gly Leu Cys Gly Asn Tyr Asn Gly Asn Gln Gly Asp Asp
            500                 505                 510

Phe Leu Thr Pro Ser Gly Leu Ala Glu Pro Arg Val Glu Asp Phe Gly
        515                 520                 525

Asn Ala Trp Lys Leu His Gly Asp Cys Gln Asp Leu Gln Lys Gln His
    530                 535                 540

Ser Asp Pro Cys Ala Leu Asn Pro Arg Met Thr Arg Phe Ser Glu Glu
```

-continued

```
545                 550                 555                 560

Ala Cys Ala Val Leu Thr Ser Pro Thr Phe Glu Ala Cys His Arg Ala
                565                 570                 575

Val Ser Pro Leu Pro Tyr Leu Arg Asn Cys Arg Tyr Asp Val Cys Ser
            580                 585                 590

Cys Ser Asp Gly Arg Glu Cys Leu Cys Gly Ala Leu Ala Ser Tyr Ala
        595                 600                 605

Ala Ala Cys Ala Gly Arg Gly Val Arg Val Ala Trp Arg Glu Pro Gly
    610                 615                 620

Arg Cys Glu Leu Asn Cys Pro Lys Gly Gln Val Tyr Leu Gln Cys Gly
625                 630                 635                 640

Thr Pro Cys Asn Leu Thr Cys Arg Ser Leu Ser Tyr Pro Asp Glu Glu
                645                 650                 655

Cys Asn Glu Ala Cys Leu Glu Gly Cys Phe Cys Pro Pro Gly Leu Tyr
            660                 665                 670

Met Asp Glu Arg Gly Asp Cys Val Pro Lys Ala Gln Cys Pro Cys Tyr
        675                 680                 685

Tyr Asp Gly Glu Ile Phe Gln Pro Glu Asp Ile Phe Ser Asp His His
    690                 695                 700

Thr Met Cys Tyr Cys Glu Asp Gly Phe Met His Cys Thr Met Ser Gly
705                 710                 715                 720

Val Pro Gly Ser Leu Leu Pro Asp Ala Val Leu Ser Ser Pro Leu Ser
                725                 730                 735

His Arg Ser Lys Arg Ser Leu Ser Cys Arg Pro Pro Met Val Lys Leu
            740                 745                 750

Val Cys Pro Ala Asp Asn Leu Arg Ala Glu Gly Leu Glu Cys Thr Lys
        755                 760                 765

Thr Cys Gln Asn Tyr Asp Leu Glu Cys Met Ser Met Gly Cys Val Ser
    770                 775                 780

Gly Cys Leu Cys Pro Pro Gly Met Val Arg His Glu Asn Arg Cys Val
785                 790                 795                 800

Ala Leu Glu Arg Cys Pro Cys Phe His Gln Gly Lys Glu Tyr Ala Pro
                805                 810                 815

Gly Glu Thr Val Lys Ile Gly Cys Asn Thr Cys Val Cys Arg Asp Arg
            820                 825                 830

Lys Trp Asn Cys Thr Asp His Val Cys Asp Ala Thr Cys Ser Thr Ile
        835                 840                 845

Gly Met Ala His Tyr Leu Thr Phe Asp Gly Leu Lys Tyr Leu Phe Pro
    850                 855                 860

Gly Glu Cys Gln Tyr Val Leu Val Gln Asp Tyr Cys Gly Ser Asn Pro
865                 870                 875                 880

Gly Thr Phe Arg Ile Leu Val Gly Asn Lys Gly Cys Ser His Pro Ser
                885                 890                 895

Val Lys Cys Lys Lys Arg Val Thr Ile Leu Val Glu Gly Gly Glu Ile
            900                 905                 910

Glu Leu Phe Asp Gly Glu Val Asn Val Lys Arg Pro Met Lys Asp Glu
        915                 920                 925

Thr His Phe Glu Val Val Glu Ser Gly Arg Tyr Ile Ile Leu Leu Leu
    930                 935                 940

Gly Lys Ala Leu Ser Val Val Trp Asp Arg His Leu Ser Ile Ser Val
945                 950                 955                 960

Val Leu Lys Gln Thr Tyr Gln Glu Lys Val Cys Gly Leu Cys Gly Asn
                965                 970                 975
```

-continued

Phe Asp Gly Ile Gln Asn Asn Asp Leu Thr Ser Ser Asn Leu Gln Val
980 985 990

Glu Glu Asp Pro Val Asp Phe Gly Asn Ser Trp Lys Val Ser Ser Gln
995 1000 1005

Cys Ala Asp Thr Arg Lys Val Pro Leu Asp Ser Ser Pro Ala Thr
1010 1015 1020

Cys His Asn Asn Ile Met Lys Gln Thr Met Val Asp Ser Ser Cys
1025 1030 1035

Arg Ile Leu Thr Ser Asp Val Phe Gln Asp Cys Asn Lys Leu Val
1040 1045 1050

Asp Pro Glu Pro Tyr Leu Asp Val Cys Ile Tyr Asp Thr Cys Ser
1055 1060 1065

Cys Glu Ser Ile Gly Asp Cys Ala Ala Phe Cys Asp Thr Ile Ala
1070 1075 1080

Ala Tyr Ala His Val Cys Ala Gln His Gly Lys Val Val Thr Trp
1085 1090 1095

Arg Thr Ala Thr Leu Cys Pro Gln Ser Cys Glu Glu Arg Asn Leu
1100 1105 1110

Arg Glu Asn Gly Tyr Glu Ala Glu Trp Arg Tyr Asn Ser Cys Ala
1115 1120 1125

Pro Ala Cys Gln Val Thr Cys Gln His Pro Glu Pro Leu Ala Cys
1130 1135 1140

Pro Val Gln Cys Val Glu Gly Cys His Ala His Cys Pro Pro Gly
1145 1150 1155

Lys Ile Leu Asp Glu Leu Leu Gln Thr Cys Val Asp Pro Glu Asp
1160 1165 1170

Cys Pro Val Cys Glu Val Ala Gly Arg Arg Phe Ala Ser Gly Lys
1175 1180 1185

Lys Val Thr Leu Asn Pro Ser Asp Pro Glu His Cys Gln Ile Cys
1190 1195 1200

His Cys Asp Val Val Asn Leu Thr Cys Glu Ala Cys Gln Glu Pro
1205 1210 1215

Gly Gly Leu Val Val Pro Pro Asp Lys Thr His Thr Cys Pro Pro
1220 1225 1230

Cys Pro Ala Pro Glu Leu Leu Gly Gly Pro Ser Val Phe Leu Phe
1235 1240 1245

Pro Pro Lys Pro Lys Asp Thr Leu Met Ile Ser Arg Thr Pro Glu
1250 1255 1260

Val Thr Cys Val Val Val Asp Val Ser His Glu Asp Pro Glu Val
1265 1270 1275

Lys Phe Asn Trp Tyr Val Asp Gly Val Glu Val His Asn Ala Lys
1280 1285 1290

Thr Lys Pro Arg Glu Glu Gln Tyr Asn Ser Thr Tyr Arg Val Val
1295 1300 1305

Ser Val Leu Thr Val Leu His Gln Asp Trp Leu Asn Gly Lys Glu
1310 1315 1320

Tyr Lys Cys Lys Val Ser Asn Lys Ala Leu Pro Ala Pro Ile Glu
1325 1330 1335

Lys Thr Ile Ser Lys Ala Lys Gly Gln Pro Arg Glu Pro Gln Val
1340 1345 1350

Tyr Thr Leu Pro Pro Ser Arg Asp Glu Leu Thr Lys Asn Gln Val
1355 1360 1365

Ser Leu Thr Cys Leu Val Lys Gly Phe Tyr Pro Ser Asp Ile Ala
1370 1375 1380

Val Glu Trp Glu Ser Asn Gly Gln Pro Glu Asn Asn Tyr Lys Thr
1385 1390 1395

Thr Pro Pro Val Leu Asp Ser Asp Gly Ser Phe Phe Leu Tyr Ser
1400 1405 1410

Lys Leu Thr Val Asp Lys Ser Arg Trp Gln Gln Gly Asn Val Phe
1415 1420 1425

Ser Cys Ser Val Met His Glu Ala Leu His Asn His Tyr Thr Gln
1430 1435 1440

Lys Ser Leu Ser Leu Ser Pro Gly Lys
1445 1450

<210> SEQ ID NO 17
<211> LENGTH: 711
<212> TYPE: PRT
<213> ORGANISM: Homo sapiens

<400> SEQUENCE: 17

Ser Leu Ser Cys Arg Pro Pro Met Val Lys Leu Val Cys Pro Ala Asp
1 5 10 15

Asn Leu Arg Ala Glu Gly Leu Glu Cys Thr Lys Thr Cys Gln Asn Tyr
20 25 30

Asp Leu Glu Cys Met Ser Met Gly Cys Val Ser Gly Cys Leu Cys Pro
35 40 45

Pro Gly Met Val Arg His Glu Asn Arg Cys Val Ala Leu Glu Arg Cys
50 55 60

Pro Cys Phe His Gln Gly Lys Glu Tyr Ala Pro Gly Glu Thr Val Lys
65 70 75 80

Ile Gly Cys Asn Thr Cys Val Cys Arg Asp Arg Lys Trp Asn Cys Thr
85 90 95

Asp His Val Cys Asp Ala Thr Cys Ser Thr Ile Gly Met Ala His Tyr
100 105 110

Leu Thr Phe Asp Gly Leu Lys Tyr Leu Phe Pro Gly Glu Cys Gln Tyr
115 120 125

Val Leu Val Gln Asp Tyr Cys Gly Ser Asn Pro Gly Thr Phe Arg Ile
130 135 140

Leu Val Gly Asn Lys Gly Cys Ser His Pro Ser Val Lys Cys Lys Lys
145 150 155 160

Arg Val Thr Ile Leu Val Glu Gly Gly Glu Ile Glu Leu Phe Asp Gly
165 170 175

Glu Val Asn Val Lys Arg Pro Met Lys Asp Glu Thr His Phe Glu Val
180 185 190

Val Glu Ser Gly Arg Tyr Ile Ile Leu Leu Leu Gly Lys Ala Leu Ser
195 200 205

Val Val Trp Asp Arg His Leu Ser Ile Ser Val Val Leu Lys Gln Thr
210 215 220

Tyr Gln Glu Lys Val Cys Gly Leu Cys Gly Asn Phe Asp Gly Ile Gln
225 230 235 240

Asn Asn Asp Leu Thr Ser Ser Asn Leu Gln Val Glu Glu Asp Pro Val
245 250 255

Asp Phe Gly Asn Ser Trp Lys Val Ser Ser Gln Cys Ala Asp Thr Arg
260 265 270

Lys Val Pro Leu Asp Ser Ser Pro Ala Thr Cys His Asn Asn Ile Met
275 280 285

```
Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Asp Lys Thr His Thr Cys Pro Pro Cys Pro Ala Pro
                485                 490                 495

Glu Leu Leu Gly Gly Pro Ser Val Phe Leu Phe Pro Pro Lys Pro Lys
            500                 505                 510

Asp Thr Leu Met Ile Ser Arg Thr Pro Glu Val Thr Cys Val Val Val
        515                 520                 525

Asp Val Ser His Glu Asp Pro Glu Val Lys Phe Asn Trp Tyr Val Asp
    530                 535                 540

Gly Val Glu Val His Asn Ala Lys Thr Lys Pro Arg Glu Glu Gln Tyr
545                 550                 555                 560

Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
            580                 585                 590

Pro Ala Pro Ile Glu Lys Thr Ile Ser Lys Ala Lys Gly Gln Pro Arg
        595                 600                 605

Glu Pro Gln Val Tyr Thr Leu Pro Pro Ser Arg Asp Glu Leu Thr Lys
    610                 615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
            660                 665                 670

Lys Leu Thr Val Asp Lys Ser Arg Trp Gln Gln Gly Asn Val Phe Ser
        675                 680                 685

Cys Ser Val Met His Glu Ala Leu His Asn His Tyr Thr Gln Lys Ser
    690                 695                 700
```

Leu Ser Leu Ser Pro Gly Lys
705 710

<210> SEQ ID NO 18
<211> LENGTH: 1452
<212> TYPE: PRT
<213> ORGANISM: Homo sapiens

<400> SEQUENCE: 18

Ala Glu Gly Thr Arg Gly Arg Ser Ser Thr Ala Arg Cys Ser Leu Phe
1 5 10 15

Gly Ser Asp Phe Val Asn Thr Phe Asp Gly Ser Met Tyr Ser Phe Ala
20 25 30

Gly Tyr Cys Ser Tyr Leu Leu Ala Gly Gly Cys Gln Lys Arg Ser Phe
35 40 45

Ser Ile Ile Gly Asp Phe Gln Asn Gly Lys Arg Val Ser Leu Ser Val
50 55 60

Tyr Leu Gly Glu Phe Phe Asp Ile His Leu Phe Val Asn Gly Thr Val
65 70 75 80

Thr Gln Gly Asp Gln Arg Val Ser Met Pro Tyr Ala Ser Lys Gly Leu
85 90 95

Tyr Leu Glu Thr Glu Ala Gly Tyr Tyr Lys Leu Ser Gly Glu Ala Tyr
100 105 110

Gly Phe Val Ala Arg Ile Asp Gly Ser Gly Asn Phe Gln Val Leu Leu
115 120 125

Ser Asp Arg Tyr Phe Asn Lys Thr Cys Gly Leu Cys Gly Asn Phe Asn
130 135 140

Ile Phe Ala Glu Asp Asp Phe Met Thr Gln Glu Gly Thr Leu Thr Ser
145 150 155 160

Asp Pro Tyr Asp Phe Ala Asn Ser Trp Ala Leu Ser Ser Gly Glu Gln
165 170 175

Trp Cys Glu Arg Ala Ser Pro Pro Ser Ser Ser Cys Asn Ile Ser Ser
180 185 190

Gly Glu Met Gln Lys Gly Leu Trp Glu Gln Cys Gln Leu Leu Lys Ser
195 200 205

Thr Ser Val Phe Ala Arg Cys His Pro Leu Val Asp Pro Glu Pro Phe
210 215 220

Val Ala Leu Cys Glu Lys Thr Leu Cys Glu Cys Ala Gly Gly Leu Glu
225 230 235 240

Cys Ala Cys Pro Ala Leu Leu Glu Tyr Ala Arg Thr Cys Ala Gln Glu
245 250 255

Gly Met Val Leu Tyr Gly Trp Thr Asp His Ser Ala Cys Ser Pro Val
260 265 270

Cys Pro Ala Gly Met Glu Tyr Arg Gln Cys Val Ser Pro Cys Ala Arg
275 280 285

Thr Cys Gln Ser Leu His Ile Asn Glu Met Cys Gln Glu Arg Cys Val
290 295 300

Asp Gly Cys Ser Cys Pro Glu Gly Gln Leu Leu Asp Glu Gly Leu Cys
305 310 315 320

Val Glu Ser Thr Glu Cys Pro Cys Val His Ser Gly Lys Arg Tyr Pro
325 330 335

Pro Gly Thr Ser Leu Ser Arg Asp Cys Asn Thr Cys Ile Cys Arg Asn
340 345 350

Ser Gln Trp Ile Cys Ser Asn Glu Glu Cys Pro Gly Glu Cys Leu Val
355 360 365

-continued

Thr Gly Gln Ser His Phe Lys Ser Phe Asp Asn Arg Tyr Phe Thr Phe
    370                 375                 380

Ser Gly Ile Cys Gln Tyr Leu Leu Ala Arg Asp Cys Gln Asp His Ser
385                 390                 395                 400

Phe Ser Ile Val Ile Glu Thr Val Gln Cys Ala Asp Asp Arg Asp Ala
                405                 410                 415

Val Cys Thr Arg Ser Val Thr Val Arg Leu Pro Gly Leu His Asn Ser
            420                 425                 430

Leu Val Lys Leu Lys His Gly Ala Gly Val Ala Met Asp Gly Gln Asp
        435                 440                 445

Ile Gln Leu Pro Leu Leu Lys Gly Asp Leu Arg Ile Gln His Thr Val
    450                 455                 460

Thr Ala Ser Val Arg Leu Ser Tyr Gly Glu Asp Leu Gln Met Asp Trp
465                 470                 475                 480

Asp Gly Arg Gly Arg Leu Leu Val Lys Leu Ser Pro Val Tyr Ala Gly
                485                 490                 495

Lys Thr Cys Gly Leu Cys Gly Asn Tyr Asn Gly Asn Gln Gly Asp Asp
            500                 505                 510

Phe Leu Thr Pro Ser Gly Leu Ala Glu Pro Arg Val Glu Asp Phe Gly
        515                 520                 525

Asn Ala Trp Lys Leu His Gly Asp Cys Gln Asp Leu Gln Lys Gln His
    530                 535                 540

Ser Asp Pro Cys Ala Leu Asn Pro Arg Met Thr Arg Phe Ser Glu Glu
545                 550                 555                 560

Ala Cys Ala Val Leu Thr Ser Pro Thr Phe Glu Ala Cys His Arg Ala
                565                 570                 575

Val Ser Pro Leu Pro Tyr Leu Arg Asn Cys Arg Tyr Asp Val Cys Ser
            580                 585                 590

Cys Ser Asp Gly Arg Glu Cys Leu Cys Gly Ala Leu Ala Ser Tyr Ala
        595                 600                 605

Ala Ala Cys Ala Gly Arg Gly Val Arg Val Ala Trp Arg Glu Pro Gly
    610                 615                 620

Arg Cys Glu Leu Asn Cys Pro Lys Gly Gln Val Tyr Leu Gln Cys Gly
625                 630                 635                 640

Thr Pro Cys Asn Leu Thr Cys Arg Ser Leu Ser Tyr Pro Asp Glu Glu
                645                 650                 655

Cys Asn Glu Ala Cys Leu Glu Gly Cys Phe Cys Pro Pro Gly Leu Tyr
            660                 665                 670

Met Asp Glu Arg Gly Asp Cys Val Pro Lys Ala Gln Cys Pro Cys Tyr
        675                 680                 685

Tyr Asp Gly Glu Ile Phe Gln Pro Glu Asp Ile Phe Ser Asp His His
    690                 695                 700

Thr Met Cys Tyr Cys Glu Asp Gly Phe Met His Cys Thr Met Ser Gly
705                 710                 715                 720

Val Pro Gly Ser Leu Leu Pro Asp Ala Val Leu Ser Ser Pro Leu Ser
                725                 730                 735

His Arg Ser Lys Arg Ser Leu Ser Cys Arg Pro Pro Met Val Lys Leu
            740                 745                 750

Val Cys Pro Ala Asp Asn Leu Arg Ala Glu Gly Leu Glu Cys Thr Lys
        755                 760                 765

Thr Cys Gln Asn Tyr Asp Leu Glu Cys Met Ser Met Gly Cys Val Ser
    770                 775                 780

-continued

```
Gly Cys Leu Cys Pro Pro Gly Met Val Arg His Glu Asn Arg Cys Val
785                 790                 795                 800

Ala Leu Glu Arg Cys Pro Cys Phe His Gln Gly Lys Glu Tyr Ala Pro
                805                 810                 815

Gly Glu Thr Val Lys Ile Gly Cys Asn Thr Cys Val Cys Arg Asp Arg
            820                 825                 830

Lys Trp Asn Cys Thr Asp His Val Cys Asp Ala Thr Cys Ser Thr Ile
        835                 840                 845

Gly Met Ala His Tyr Leu Thr Phe Asp Gly Leu Lys Tyr Leu Phe Pro
    850                 855                 860

Gly Glu Cys Gln Tyr Val Leu Val Gln Asp Tyr Cys Gly Ser Asn Pro
865                 870                 875                 880

Gly Thr Phe Arg Ile Leu Val Gly Asn Lys Gly Cys Ser His Pro Ser
                885                 890                 895

Val Lys Cys Lys Lys Arg Val Thr Ile Leu Val Glu Gly Gly Glu Ile
            900                 905                 910

Glu Leu Phe Asp Gly Glu Val Asn Val Lys Arg Pro Met Lys Asp Glu
        915                 920                 925

Thr His Phe Glu Val Val Glu Ser Gly Arg Tyr Ile Ile Leu Leu Leu
    930                 935                 940

Gly Lys Ala Leu Ser Val Val Trp Asp Arg His Leu Ser Ile Ser Val
945                 950                 955                 960

Val Leu Lys Gln Thr Tyr Gln Glu Lys Val Cys Gly Leu Cys Gly Asn
                965                 970                 975

Phe Asp Gly Ile Gln Asn Asn Asp Leu Thr Ser Ser Asn Leu Gln Val
            980                 985                 990

Glu Glu Asp Pro Val Asp Phe Gly  Asn Ser Trp Lys Val  Ser Ser Gln
        995                 1000                1005

Cys Ala  Asp Thr Arg Lys Val  Pro Leu Asp Ser Ser  Pro Ala Thr
    1010                1015                1020

Cys His  Asn Asn Ile Met Lys  Gln Thr Met Val Asp  Ser Ser Cys
    1025                1030                1035

Arg Ile  Leu Thr Ser Asp Val  Phe Gln Asp Cys Asn  Lys Leu Val
    1040                1045                1050

Asp Pro  Glu Pro Tyr Leu Asp  Val Cys Ile Tyr Asp  Thr Cys Ser
    1055                1060                1065

Cys Glu  Ser Ile Gly Asp Cys  Ala Cys Phe Cys Asp  Thr Ile Ala
    1070                1075                1080

Ala Tyr  Ala His Val Cys Ala  Gln His Gly Lys Val  Val Thr Trp
    1085                1090                1095

Arg Thr  Ala Thr Leu Cys Pro  Gln Ser Cys Glu Glu  Arg Asn Leu
    1100                1105                1110

Arg Glu  Asn Gly Tyr Glu Cys  Glu Trp Arg Tyr Asn  Ser Cys Ala
    1115                1120                1125

Pro Ala  Cys Gln Val Thr Cys  Gln His Pro Glu Pro  Leu Ala Cys
    1130                1135                1140

Pro Val  Gln Cys Val Glu Gly  Cys His Ala His Cys  Pro Pro Gly
    1145                1150                1155

Lys Ile  Leu Asp Glu Leu Leu  Gln Thr Cys Val Asp  Pro Glu Asp
    1160                1165                1170

Cys Pro  Val Cys Glu Val Ala  Gly Arg Arg Phe Ala  Ser Gly Lys
    1175                1180                1185

Lys Val  Thr Leu Asn Pro Ser  Asp Pro Glu His Cys  Gln Ile Cys
```

-continued

```
    1190                1195                1200

His Cys  Asp Val Val Asn Leu  Thr Cys Glu Ala Cys  Gln Glu Pro
    1205                1210                1215

Gly Gly  Leu Val Val Pro Pro  Asp Lys Thr His Thr  Cys Pro Pro
    1220                1225                1230

Cys Pro  Ala Pro Glu Leu Leu  Gly Gly Pro Ser Val  Phe Leu Phe
    1235                1240                1245

Pro Pro  Lys Pro Lys Asp Thr  Leu Met Ile Ser Arg  Thr Pro Glu
    1250                1255                1260

Val Thr  Cys Val Val Val Asp  Val Ser His Glu Asp  Pro Glu Val
    1265                1270                1275

Lys Phe  Asn Trp Tyr Val Asp  Gly Val Glu Val His  Asn Ala Lys
    1280                1285                1290

Thr Lys  Pro Arg Glu Glu Gln  Tyr Asn Ser Thr Tyr  Arg Val Val
    1295                1300                1305

Ser Val  Leu Thr Val Leu His  Gln Asp Trp Leu Asn  Gly Lys Glu
    1310                1315                1320

Tyr Lys  Cys Lys Val Ser Asn  Lys Ala Leu Pro Ala  Pro Ile Glu
    1325                1330                1335

Lys Thr  Ile Ser Lys Ala Lys  Gly Gln Pro Arg Glu  Pro Gln Val
    1340                1345                1350

Tyr Thr  Leu Pro Pro Ser Arg  Asp Glu Leu Thr Lys  Asn Gln Val
    1355                1360                1365

Ser Leu  Thr Cys Leu Val Lys  Gly Phe Tyr Pro Ser  Asp Ile Ala
    1370                1375                1380

Val Glu  Trp Glu Ser Asn Gly  Gln Pro Glu Asn Asn  Tyr Lys Thr
    1385                1390                1395

Thr Pro  Pro Val Leu Asp Ser  Asp Gly Ser Phe Phe  Leu Tyr Ser
    1400                1405                1410

Lys Leu  Thr Val Asp Lys Ser  Arg Trp Gln Gln Gly  Asn Val Phe
    1415                1420                1425

Ser Cys  Ser Val Met His Glu  Ala Leu His Asn His  Tyr Thr Gln
    1430                1435                1440

Lys Ser  Leu Ser Leu Ser Pro  Gly Lys
    1445                1450
```

VECTOR CO-EXPRESSING TRUNCATED VON WILLEBRAND FACTOR AND FACTOR VIII

FIELD OF THE INVENTION

The present invention relates to a co-expression vector that comprises both truncated von Willebrand Factor (vWF)-Fc DNA construct and B-domain deleted FVIII DNA construct in the same vector.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Mar. 28, 2019, and a size of 129 kilobytes. The Sequence Listing filed via EFS-Web is part of the specification and is hereby incorporated in its entirety by reference herein.

BACKGROUND

Blood clotting proceeds through a complex and dynamic biological pathway of interdependent biochemical reactions, referred to as the coagulation cascade, in which three pathways, the extrinsic pathway, the intrinsic pathway and the common pathway are included. Factor VIII (FVIII) is a glycoprotein, circulating as an inactive cofactor with full-length von Willebrand factor (vWF) in plasma in 1:50 ratio, that plays a critical role in the intrinsic pathway for maintaining normal hemostasis. Full-length FVIII is a non-covalently bound heterodimer comprised of a heavy chain (A1-A2-B domains) and light chain (A3-C1-C2 domains). In response to injury, the activated form of factor VIII separates from vWF and forms a complex with factor IXa and Factor X (so-called Xase complex) on the charged phospholipid membranes provided by activated platelets. The Xase complex further activates Factor V (FV) to generate FVa, which in turn activates prothrombin to thrombin together with Factor Xa and other components in the coagulation cascade to generate a stable clot.

Hemophilia A is a congenital X chromosome-linked bleeding disorder characterized by a deficiency in FVIII activity. Diminished FVIII activity inhibits the positive feedback loop in the coagulation cascade, ultimately leading to bleeding episodes with increased duration, extensive bruising, spontaneous oral and nasal bleeding, joint stiffness and chronic pain, and possibly internal bleeding and anemia, in severe cases. The most common treatment for Hemophilia A is replacement therapy with either human plasma-derived or recombinant FVIII through intravenous administration.

High production of recombinant FVIII (rFVIII) in mammalian cells has been found to be difficult. The large molecular weight of this protein (~300 kDa), the complexity of the post-translational modifications required (e.g., numerous glycosylation and tyrosine sulfation sites), and the limits of expression elements (like mRNA instability) make the high production of rFVIII a challenge. Removal of the central B-domain has greatly improved rFVIII production, but the commercial production level of rFVIII is still generally in the range of 20-50 IU/ml. Additional possible factors contributing to the low expression level of the recombinant FVIII in mammalian cells may include, specifically or non-specifically, binding to expression cell membranes and FVIII instability (Kaufman, 1989, Mol. Cell. Biol., vol. 3, pp. 1233-1242: U.S. Pat. No. 8,759,293).

U.S. Pat. No. 8,759,293 discloses a method for preparing FVIII. FIG. 6 of the '293 Patent illustrates a first plasmid expression vector that expresses (i) mature vWF or truncated vWF domain-Fc fusion polypeptides, and (ii) propeptide sequences from independent promoters, and a second and a different plasmid expression vector the expresses (iii) human FVIII using a different selectable marker. The first and the second plasmids are co-transfected and taken up into mammalian cells under selection to create a stable cell line that expresses (i) vWF or vWF-Fc, (ii) vWF propeptide, and (iii) FVIII. The problem for this method is that each selected cell transfectant is obtained by independent and separate entry of FVIII and vWF-Fc plasmids into a mammalian cell. Selected cells can have different ratios of each plasmid. It is difficult to obtain cells reliably and reproducibly with consistent expression of proteins if the ratio of the transfected plasmids is unknown, and thus the absolute levels of the expressed proteins will change over time. For example, a primary cell transfectant produced by sequential transfection may have 10 copies of FVIII and 30 copies of vWF-Fc. Over-expression of vWF-Fc over FVIII, would result in excessive quantities of vWF-Fc relative to FVIII, and thus make downstream purification of FVIII difficult. Further, if the ratio of the two plasmids changes over time, a cell may become undesirable due to reduction in FVIII plasmids, while maintaining a constant number of vWF plasmids. The loss of one plasmid relative to another may upset the balance in expression levels, which results in difficult purification scenarios.

There is a need for improvement in the quality and quantity of recombinant FVIII available to patients. There is a need for improving the expression of FVIII and improving the yield of expressed FVIII after purification.

BRIEF DESCRIPTION OF THE DRAWINGS

FIGS. 2A-2D show a schematic representation of the derivation of a truncated human vWF-Fc protein created by fusion of a D'D3 domain to the Fc hinge domain of human $IgG_1$. (2A) Domain structure of a secreted von Willebrand factor polypeptide (signal sequence not shown). D1 and D2 represent the vWF propeptide sequence; D'D3 includes the nominal Factor VIII binding site; CK is the terminal dimerization domain of wild-type vWF. (2B1) Pro-D'D3-Fc is a truncated vWF protein consisting of the propeptide (D1D2 domains) and D'D3 domains fused to the Fc domain. (2B2) In this alternate form, the D1D2 domains are physically removed from vWF and fused directly to the signal sequence at the N-terminus of the D'D3-Fc sequence, creating Del-D'D3-Fc. (2C) With or without the presence of D1D2, a mature truncated product, namely, D'D3-Fc. (2D) Multimers of wild-type D'D3 domain are formed through disulfide bridges, while dimerization of D'D3 is mediated by interaction of the Fc fusion domain at the C-terminus.

FIGS. 3A-3D show a schematic representation of truncated human vWF-Fc protein, with mutations at amino acid position C1099 and C1142. (3A) Domain structure of a mutated and secreted von Willebrand factor polypeptide (signal sequence not shown). D1D2 are propeptide domains; D'D3 includes the nominal Factor VIII binding site, but includes mutations at amino acids C1099 and C1142 (vertical lines in D3 domain). (3B1) Pro-D'D3mut-Fc is as described above for Pro-D'D3-Fc, but contains mutations at position C1099 and C1142. (3B2) In this alternate form, the D1D2 domains are physically removed from vWF and fused directly to the signal sequence at the N-terminus of the D'D3-Fc sequence that has mutations at C1099 and C1142, resulting in Del-D'D3mut-Fc. (3C) With or without the presence of D1D2, a mature truncated product, D'D3mut-Fc. (3D) Formation of multimers of wild-type D'D3 domain is blocked by the C1099 and C1142 mutations (asterisks), while dimerization of D'D3 is mediated by interaction of the Fc fusion domain at the C-terminus.

DETAILED DESCRIPTION OF THE INVENTION

Figure 1B:
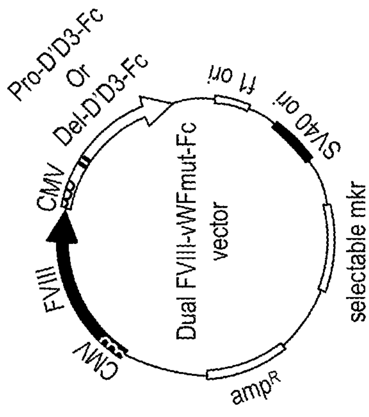
FIGS. 1A-1C illustrate the construction of a dual expression vector, in which both human FVIII and truncated, and in some cases, mutated, vWF-Fc cDNAs are subcloned juxtaposed into the same expression vector. (1A) A general representation of the dual expression vector containing FVIII and vWF-Fc variant gene sequences under control of cytomegalovirus (CMV) promoters. (1B) A representation of the co-expression of FVIII and truncated vWF (with or without the vWF propeptide domain) and fused to an immunoglobulin Fc domain (Pro-D'D3-Fc contains the propeptide domain, while Del-D'D3-Fc does not). (1C) A representation of the co-expression of FVIII and truncated and mutated vWF (at amino acids C1099 and C1142 of complete wild-type vWF sequence, according to the HGVS numbering convention, and with or without the vWF propeptide domain) and fused to an immunoglobulin Fc domain from human $IgG_1$. Other plasmid elements are also shown.

The present invention provides the solution to many of the current issues in human recombinant coagulation Factor VIII purification and production, namely, to have both FVIII and truncated vWF-Fc expression cassettes co-expressed from two independent promotors on the same expression vector with a single selectable marker gene. While the absolute expression levels of the expressed proteins might change, a desirable 1:1 ratio of FVIII:vWF-Fc expression is established, thereby minimizing the likelihood that vWF significantly overwhelms FVIII during purification, which would make recovery of FVIII problematic.

In addition to controlling the relative ratios of expression genes, and their proteins, a method has been developed to improve recovery of FVIII:vWF complexes. This is done by fusing an immunoglobulin Fc region onto the C-terminus of truncated regions of human rec-vWF, specifically, the D'D3 region that binds FVIII (ca. aa 776-1241). In addition, however, the vWF-Fc domains are created by direct fusion to a signal sequence to promote efficient processing, and further, has been modified with specific mutations to promote higher ratios of FVIII:vWF complexes. The fusion with Fc provides a straightforward method to select FVIII-vWF complexes from the bulk of the cell supernatant, by virtue of the ability of Fc regions to bind to staphylococcal-derived protein A, anti-Fc antibody, etc., that are immobilized on solid matrices. Naturally, other methods can used to achieve a similar result, but a preferred C-terminal fusion partner is immunoglobulin Fc as it also facilitates truncated vWF fragment dimerization, that is important for FVIII binding (Chiu et al., 2015, Blood, vol. 126, pp. 935-938 and Yee et al., 2015, Blood, vol. 126, pp. 939-942). The potential issue of expressing wild-type truncated vWF-Fc is that the truncated vWF-Fc proteins engage in normal head-to-head and tail-to-tail multimerization through one or two specific cysteine residues in the D'D3 domains, as well as through the dimerization of Fc domains. Recombinant vWF-Fc polymers can thus yield long molecules as long as 50 polypeptide units in length, and covalently-linked; typically, they are in the size range of about 20-25 polypeptide units. Such size ranges represent molecular weights of 5-10 million daltons, or more, that become problematic for large-scale column purification typically employed for preparing proteins, especially on a commercial scale. The large size of such complexes can create tangles or aggregates that often block column flow, create excessive back-pressure, and make recovery of the desired proteins difficult.

The present invention solves this problem by including mutations at certain cysteine amino acids in the D'D3 domain, specifically, at amino acids C1099 and C1142 of vWF polypeptide. These amino acids appear to be important in driving inter-molecular disulfide bridges between D'D3 dimers, but do not appear to be critical for FVIII binding. As such, using mutations introduced into the D'D3 domain of vWF-Fc should prevent multimer assembly, and limit the size of the D'D3 domains to monomers or dimers, especially at high concentrations of expressed protein. This is ideal for large-scale column purification and preventing clogging of depth-filtration columns, affinity columns, etc., and will yield better recovery and purity of FVIII.

An additional modification disclosed in the present invention can further enhance both expression and purification-elimination of the gene sequence encompassing the vWF propeptide domain from the expression cassette encoding truncated vWF-Fc. This propeptide normally remains associated with, and helps to fold, vWF after cleavage in, and transit from, the Golgi apparatus—it is included in expression of mammalian vWF proteins in cell-based systems. However, large amounts of vWF that are expressed in mammalian systems are inefficiently processed by the furin/Kex2-like proteases that are present (or insufficiently present) in mammalian cells; as a consequence, unprocessed propeptide still attached to "mature" vWF protein, or truncated fragments, can further complicate the large size of vWF multimers that may be formed, and render purification difficult.

The present invention removes the propeptide sequence from the vWF expression cassette and solves this problem by eliminating the need for the furin/Kex2-like proteins: mature domains are expressed directly by cleavage of the pre-protein from its signal peptide. Despite the absence of the propeptide in the folding of vWF domains, the fused Fc domain provides sufficient folding to drive dimerization of the D'D3 sequence that binds to FVIII. Elimination of the propeptide sequence further reduces the cassette size in expression vectors and allows for better expression in mammalian cells.

The present invention uses a single DNA expression vector comprising DNA constructs of recombinant FVIII and its modified binding partner protein, i.e., truncated, recombinant von Willebrand factor (vWF), to co-express the two proteins in mammalian cells, at very high expression levels of FVIII.

Four different truncated vWF-Fc DNA cassettes, each having a nucleotide sequence that encodes a truncated vWF-Fc fusion protein, are inserted into the expression plasmid vector; truncated vWF-Fc constructs are defined as follows: (a) Pro-D'D3-Fc represents a construct that contains vWF propeptide domain (D1D2, comprising amino acids+1-741 of the wild-type vWF molecule) and domains D'D3 (comprising amino acids 742-1247 of the wild-type vWF molecule), fused at its C-terminus with an immunoglobulin Fc domain from human $IgG_1$ (e.g., UniProtKB 01857, comprising amino acids 104-330); (b) Del-D'D3-Fc represents a construct that contains vWF domains D'D3 (comprising amino acids 742-1247 of the wild-type vWF molecule), fused at its C-terminus with an immunoglobulin Fc domain from human $IgG_1$ (e.g., UniProtKB 01857, comprising amino acids 104-330); in contrast to construct (a) above, the propeptide domain (D1D2) has been deleted in this construct; (c) Pro-D'D3mut-Fc represents a construct that contains vWF propeptide domain (D1D2, comprising amino acids+1-741 of the wild-type vWF molecule) and domains D'D3, amino acids of the wild-type vWF molecule, but with mutations at C1099 and C1142 of the complete vWF molecule (including its signal sequence; numbering is according to the Human Genome Variant Society (HGVS) numbering convention), fused at its C-terminus with an immunoglobulin Fc domain from human $IgG_1$ (e.g., UniProtKB 01857, comprising amino acids 104-330); and (d) Del-D'D3mut-Fc represents a construct that contains vWF domains D'D3 (comprising amino acids 742-1247 of the wild-type vWF molecule) but with mutations at C1099 and C1142 of the complete vWF molecule (including its signal sequence; numbering is according to the HGVS numbering convention), fused at its C-terminus with an immunoglobulin Fc domain from human $IgG_1$ (e.g., UniProtKB 01857, comprising amino acids 104-330), but in contrast to construct (c), the propeptide domain (D1D2) has been deleted in this construct.

vWF and FVIII polypeptides of human and non-human (e.g., primates, dogs, cats, horses, pigs, mice, rats, guinea pigs, rabbits, cows, other vertebrates) origin are contemplated by the present invention, which include natural, synthetic, and recombinant proteins. Also within the scope of the present invention are vWF and FVIII polypeptides corresponding to wild-type proteins, or mutants, variants, and/or truncations thereof.

Figures 2A, 2C, 2D:
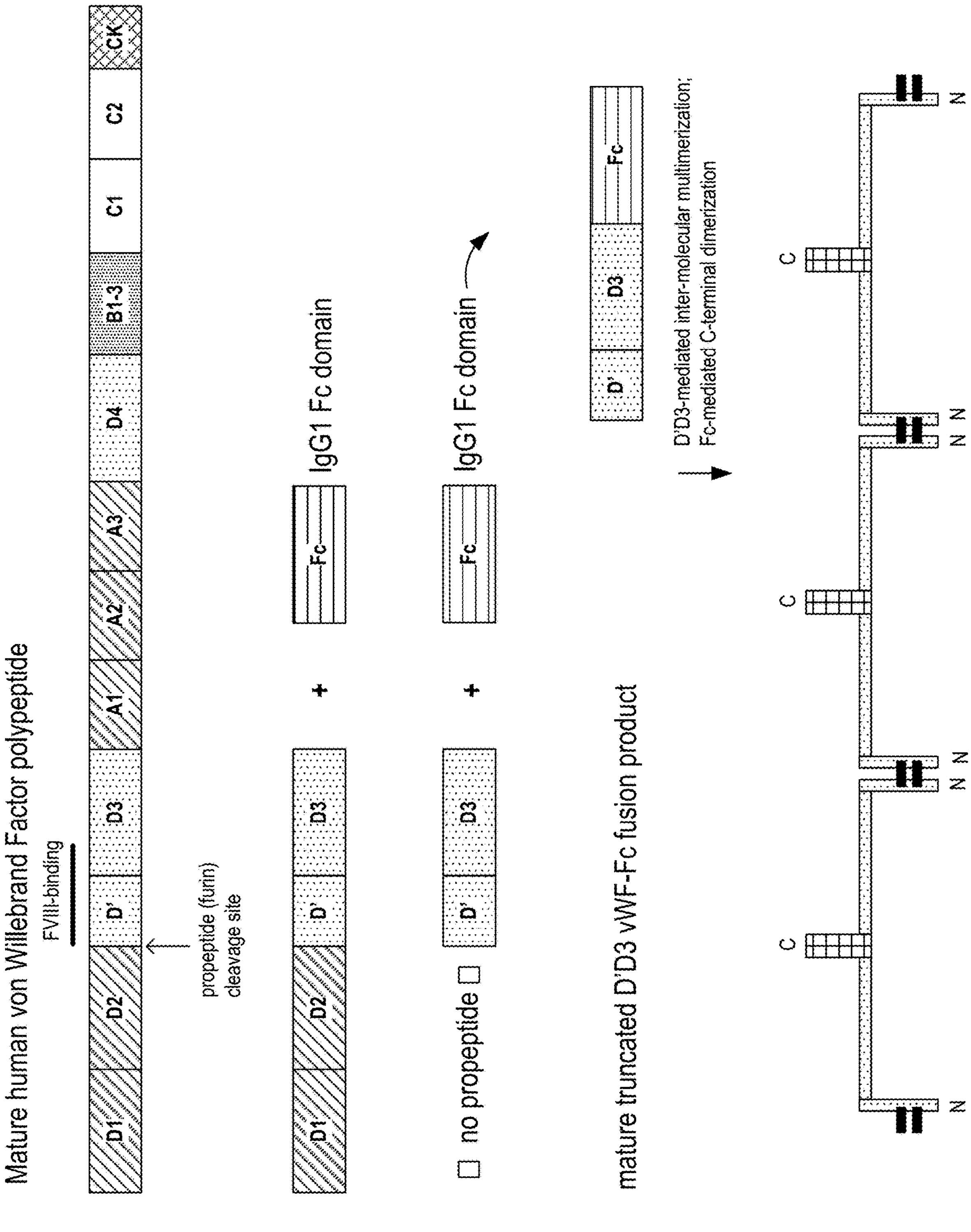
Figures 3A, 3C, 3D:
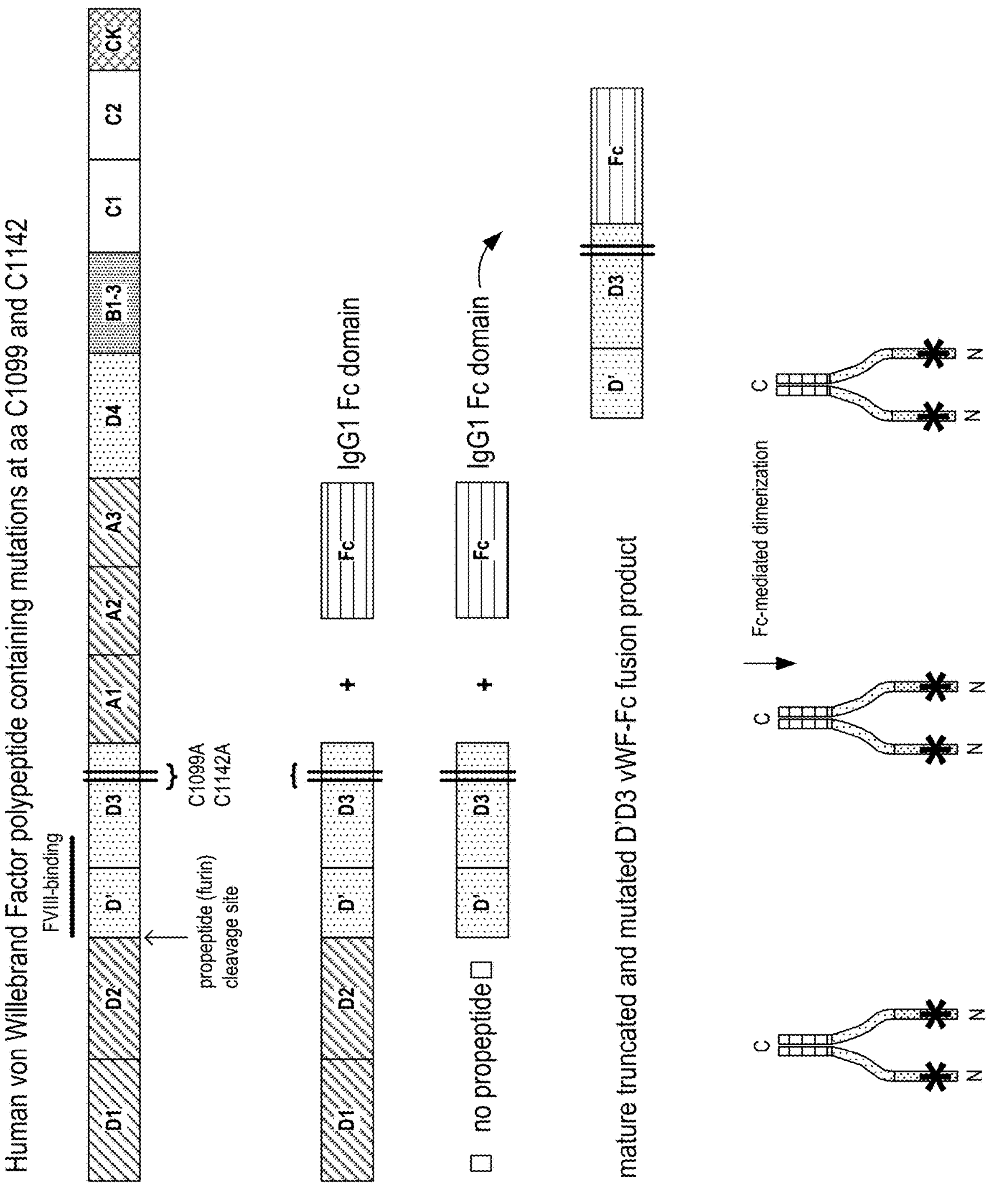
Figure 4A:
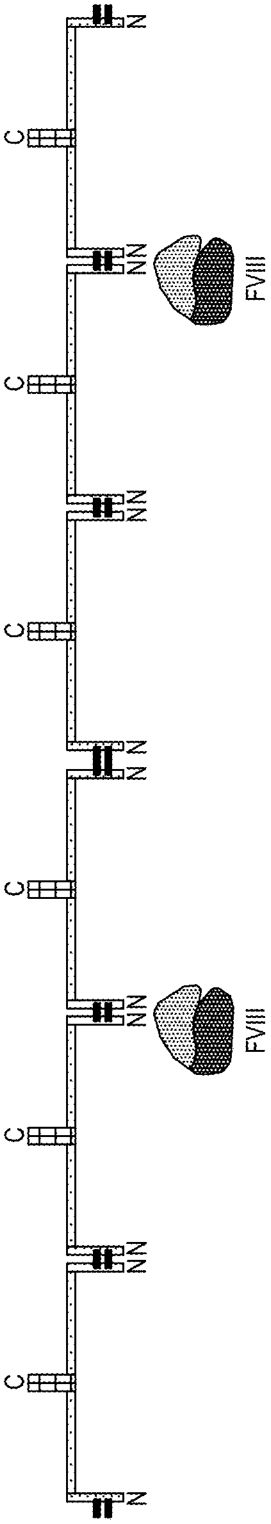
FIGS. 4A-4B show a representation of the assembly of D'D3-Fc and D'D3mut-Fc proteins, with FVIII. (4A) D'D3-Fc (no introduced mutations) results in multimer assembly and dimerization as described in FIG. 3. As an example, binding to FVIII is shown at two sites on multimerized D'D3-Fc molecule. (4B) D'D3mut-Fc fusion protein is expected to result in assembly of dimers instead of multimers, due to introduced mutations C1099 and C1142 (shown as an asterisk).
Figure 4B:
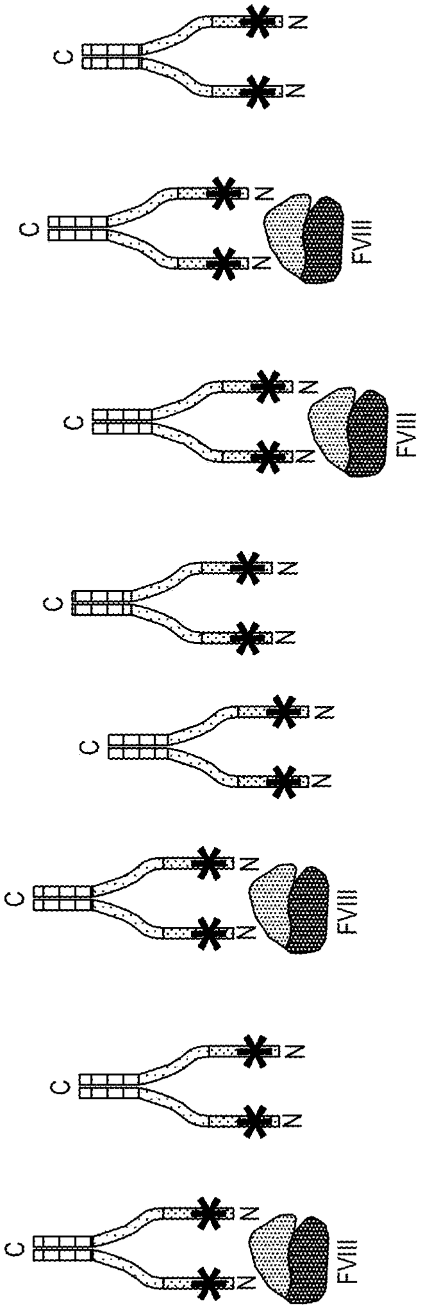
Figure 5B:
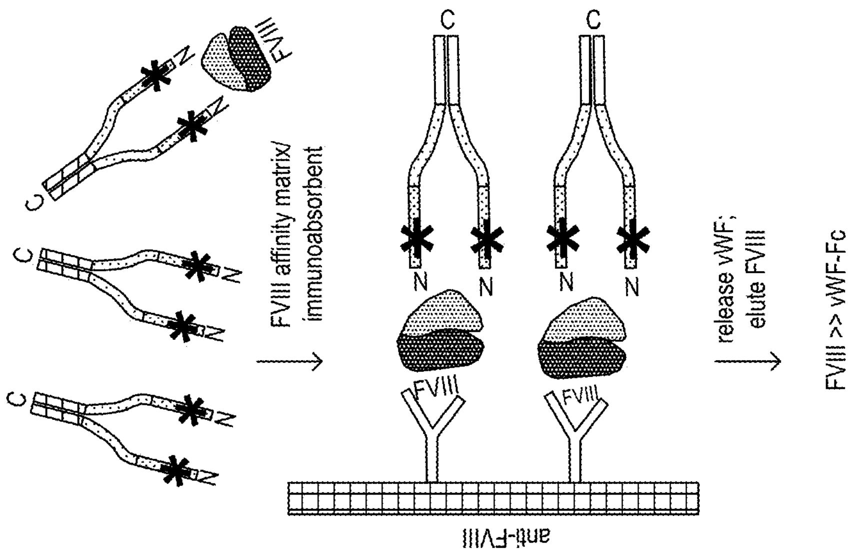
FIGS. 5A-5B illustrate differences in the likely capture and recovery of FVIII/truncated vWF-Fc complexes due to differences between non-mutated and mutated D'D3 variants, and consequences of purification of resulting Factor VIII though a Factor VIII affinity matrix. (5A) Multimers D'D3-Fc that bind to FVIII are shown. FVIII binds to a purification matrix through binding interactions to an affinity ligand and is retained along with D'D3-Fc on the column. FVIII eluted from such a column is probably heavily contaminated with D'D3-Fc, so that [FVIII]<[D'D3-Fc]. (5B) Dimeric forms of D'D3mut-Fc are shown to bind Factor VIII. Due to the lack of multimerization, individual FVIII/D'D3-Fc complexes are expected to bind to anti-FVIII affinity matrix efficiently, yielding a significantly purer population of FVIII, where [FVIII]>>[D'D3mut-Fc].
Figure 5A:
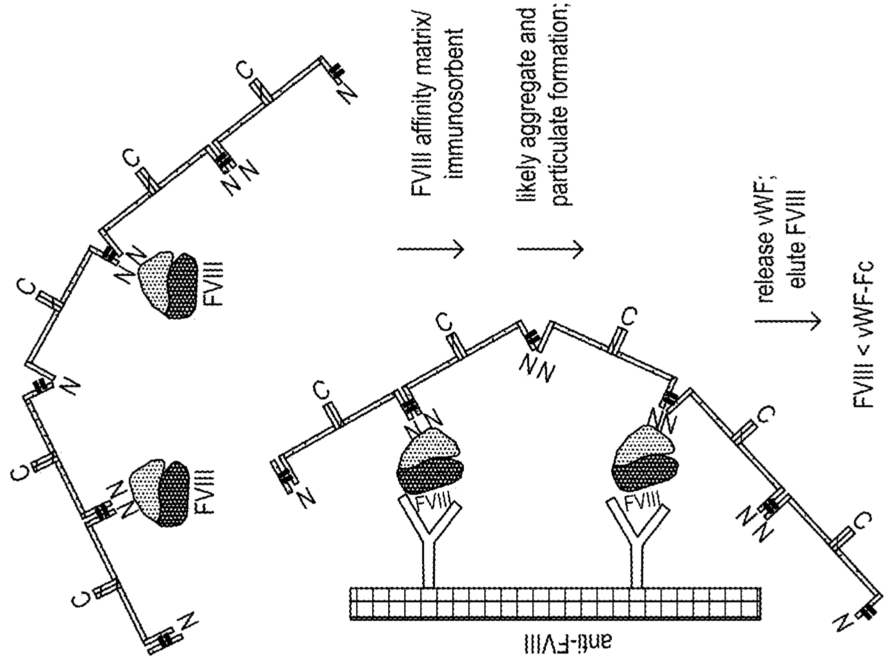
Figure 6B:
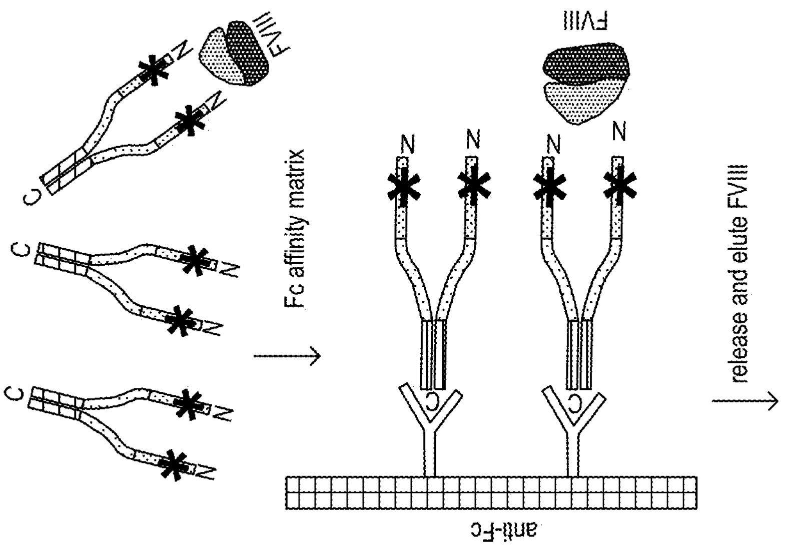
FIGS. 6A-6B show differences in the capture and recovery of FVIII-vWF-Fc complexes and the consequences of purification of resulting Factor VIII though a vWF-Fc capture matrix, similar to FIG. 5. (6A) Multimers of D'D3-Fc that bind to FVIII are shown. This could result in decreased recovery of FVIII, if D'D3-Fc is abundantly co-expressed. In addition, due to increased concentration and proximity of D'D3-Fc, FVIII may be poorly eluted from an affinity column, so that [FVIII]<<[D'D3-Fc]. (6B) Dimeric forms of D'D3mut-Fc are shown to bind FVIII are represented to bind Factor VIII. Due to the lack of multimerization, FVIII/D'D3mut-Fc complexes are expected to bind to the anti-Fc affinity matrix without aggregate formation, yielding an enriched population of FVIII binding to vWF-Fc at 1:1 ratio.
Figure 6A:
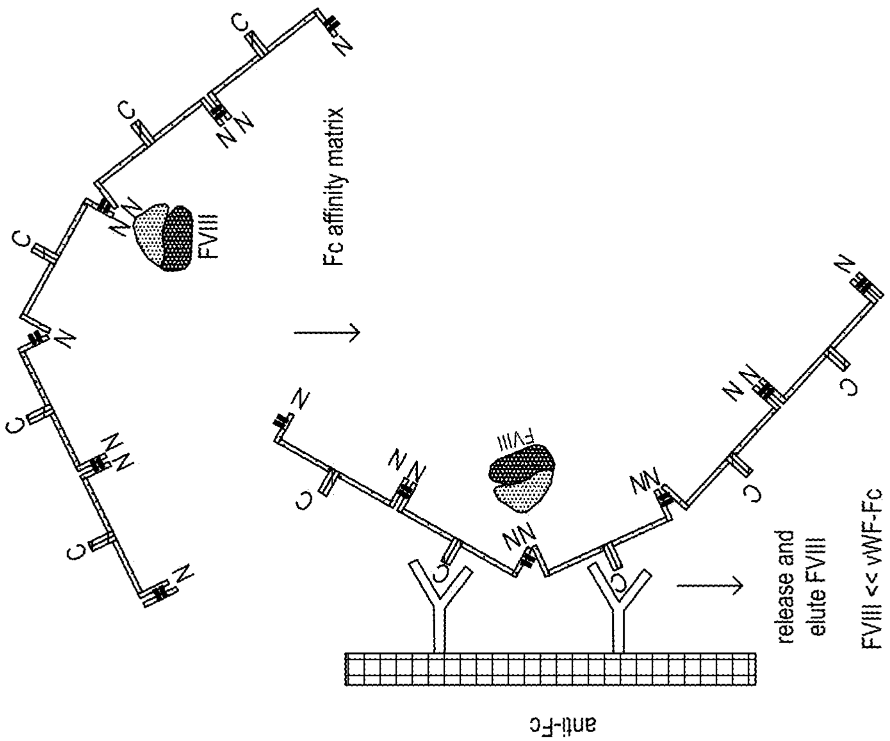

Human wild-type vWF amino acid sequence and nucleic acid sequence encoding vWF are disclosed by, e.g., GenBank Accession Nos.: NP_000543, NM_000552. Human vWF is a polypeptide of 2813 amino acids including a signal peptide of 22 amino acids and repetitive functional domains, A, B, C, D and CK, which are distributed from the amino terminal in the order D1, D2, D', D3, A1, A2, A3, D4, B1, B2, B3, C1, C2, and CK (FIG. 2A). The "mature" vWF subunit is composed of, from the N- to the C-terminus in the order, the domains D'-D3-A1-A2-A3-D4-B1-B2-B3-C1-C2-CK. Domains D1D2 (propeptide) are amino acid+1-741 of the wild-type vWF protein, and domains D'D3 are amino acids+742-1247 of the wild-type vWF protein. (+refers to signal sequence removal at the N-terminus, i.e., +1 is the first amino acid of the wild-type vWF protein without the signal sequence). D'D3 domains are recognized as the binding site for FVIII.

Human FVIII is synthesized as a single-chain molecule of approximately 300 kDa and consists of the structural domains A1-A2-B-A3-C1-C2. It is often cleaved within the B domain during secretion and circulates in the blood as a heterodimer bound to von Willebrand factor (vWF). The smallest active FVIII, with a molecular weight of 170 kD, consists of one 90 kD heavy chain which includes the A1-A2 domains, lacking the major part of the heavily glycosylated B-domain (Ser741 to Arg1648), and one 80 kD light chain including A3-C1 and C2 domains. It can be activated with thrombin to the same extent as the forms of higher molecular mass. The B-domain of FVIII is not necessary for the clotting activity of FVIII, but it was found that by deleting the B-domain, the FVIII has substantially higher expression levels from heterologous systems without impairing it's in vitro or in vivo functionality. The present invention utilizes B-domain deleted (BDD)-FVIII, wherein the two chains of FVIII are joined by a linker (SFSQNPPVLKRHQR). A human BDD FVIII sequence is shown in GenBank Protein Acc. ABV90867.

The inventors have designed A DNA vector containing dual expression cassettes to have both FVIII and truncated vWF-Fc genes co-expressed under two independent promotors. While the absolute expression levels of the expressed proteins might change, the DNA vector of the present invention may achieve a constant and desirable 1:1 ratio of FVIII to truncated vWF-Fc expression, which ensures that the level of truncated vWF-Fc protein does not significantly overwhelm the level of FVIII protein during purification, and therefore, the recovery of FVIII is under control. The expression level of FVIII produced by co-expression of FVIII and truncated vWF-Fc in one expression vector is significantly higher than those produced by other known methods.

The present invention is directed to a vector comprising: (a) a first polynucleotide sequence encoding a B-domain deleted FVIII protein (FVIII), operably linked to a first promoter, and (b) a second polynucleotide sequence encoding a fusion protein comprising a truncated von Willebrand factor (vWF) and an immunoglobulin Fc fused to the C-terminal of the truncated vWF, operably linked to a second promoter, wherein the truncated vWF comprises the amino acid sequence of SEQ ID NO: 1 [D'/D3+mutation, or Del-D'D3mut], or SEQ ID NO: 2 [D1/D2/D'/D3+mutation, or Pro-D'D3mut], or SEQ ID NO: 3 [D'/D3, or Del-D'D3], or SEQ ID NO: 4 [D1/D2/D'/D3, or Pro-D'D3], or having 95% amino acid sequence identity thereof. The first promoter and the second promoter can be the same or different. In one embodiment, the first promoter and the second promoter are the same, e.g., cytomegalovirus promoter.

In the vector of the present invention, a first polynucleotide sequence encodes a B-domain-deleted FVIII (BDD-FVIII), or an amino acid having at least 95%, or 96%, or 97%, or 98%, or 99% sequence identify thereof. The amino acid changes are preferably of a minor change such as a conservative amino acid substitution that does not significantly affect FVIII folding or binding capacity.

In the vector of the present invention, the second polynucleotide sequence encodes a fusion protein comprising a truncated vWF and an immunoglobulin Fc fused to the C-terminal of the truncated vWF, or an amino acid having at least 95%, or 96%, or 97%, or 98%, or 99% sequence identify thereof. The amino acid changes are preferably of a minor change such as a conservative amino acid substitution that does not significantly affect the binding activity of vWF to FVIII or cause multimerization of vWF. When the truncated vWF is D'D3+mutation, the amino acid substitution does not include the change of amino acid residue 1099 or 1142 (numbered according to the HGVS numbering convention) or, equivalently, 336 or 379 (counted from the N-terminus of D') back to cysteine, which negates the mutation. When the truncated vWF is D1/D2/D'/D3+mutation, the amino acid substitution does not include the change of amino acid residue 1099 or 1042 or, equivalently, 336 or 379 (counted from the N-terminus of D') back to cysteine, which negates the mutation.

To improve recovery of FVIII-vWF complexes during purification, the present invention fuses an immunoglobulin Fc region onto the C-terminus of truncated regions of human recombinant vWF, specifically, onto the D'D3 region (amino acids+742-1247 of the wild-type vWF protein). Suitable immunoglobulin Fc for the present invention includes those that can bind with high affinity to protein A or protein G or other similar Fc-binding matrices, and include the Fc regions of human IgG, murine IgG, or fragments thereof comprising at least the hinge region to facilitate the formation of interchain disulfide bonds. A preferred Fc is human IgG1 or human IgG4. For example, a preferred Fc sequence is shown in SEQ ID NO: 5, which is amino acids 104-330 of human $IgG_1$.

The fusion with Fc provides a straightforward method to select FVIII-vWF complexes from the bulk of the cell supernatant, by the ability of Fc regions to bind to its binding partner, such as staphylococcal-derived protein A, anti-Fc antibody, etc., immobilized on solid matrices. Since the truncated vWF lacks the CK domain for dimerization, the Fc portion of the vWF-Fc fusion protein also provides a mean for self-dimerization of truncated vWF-Fc through cysteines in the Fc domains.

In one embodiment, mutations are implemented into the truncated human vWF to create smaller binding complexes compared to wild-type vWF, which provide overall enhanced purification and greater in vitro stability of recombinant FVIII-vWF-Fc complexes. During secretion, vWF multimerization forms via disulfide bonds in D3 domain (C1099 and C1142), that leads to the formation of large, to extremely large, vWF molecules, typically multimers of 20-25 vWF molecules (or 20-25-mers), up to 50-mers. These size ranges represent molecular weights of at least 5-10 million daltons, which becomes problematic for large-scale column purification of FVIII. This is because the large size of such complexes can create tangles or aggregates that often block column flow and make recovery of the desired proteins difficult or impossible, while affecting the overall purity. Amino acids C1099 and C1142 (HGVS numbering) are two important residues for driving inter-molecular disulfide bridges between D'D3 domains, but they are not critical for binding to FVIII. By converting C1099 and C1142 of the D'D3 domain of vWF-Fc to A1099 and A1142, multimerization is prevented, which dramatically improves the purification and protein quality of FVIII from FVIII-vWF complexes. The cysteine mutation in domain D'D3 can be changed to alanine as shown in SEQ ID NO: 1, or other amino acids such as leucine, glycine, valine, isoleucine, phenylalaninse, serine, threonine, histidine, methionine, and possibly arginine, lysine, glutamine, asparagine, glutamic acid, aspartic acid, and tryptophan and tyrosine, but not proline, as long as the substitution for cysteine does not significantly affect the ability of the resulting vWF to bind to FVIII.

In one embodiment, the propeptide domain of vWF is deleted by elimination of the gene sequence encompassing the propeptide from the expression cassette encoding vWF-Fc. One of the functions of the propeptide is to aid in the N-terminal multimerization of vWF; the propeptide is then cleaved by furin when released into blood. However, furin/Kex-2-like proteases are often limiting in cells, so that when large amounts of vWF that are expressed in mammalian systems, they may be inefficiently processed by the furin/Kex2-like proteases, leaving uncleaved propeptide attached to vWF. This, in turn, significantly increases the molecular weight of the resulting vWF molecule and limits proper domain association. By removing of the propeptide sequence from the vWF expression cassette, the mature domains are expressed directly from its signal peptide, leading to a significant increase in vWF expression, and resulting FVIII-vWF complex formation. Despite the absence of the propeptide, the fused Fc domain provides sufficient folding to drive dimerization of the D'D3 that has higher affinity for FVIII than monomeric D'D3. Elimination of the propeptide domain further reduces the gene size in expression vectors and results in better protein expression.

Preferred B-domain deleted FVIII polypeptides for this invention include human BDD-FVIII (GenBank Protein Accession No. ABV90867, SEQ ID NO: 6), porcine BDD-FVIII, including synthetic porcine BDD-FVIII (GenBank Protein Accession No. AGV79859.1, OBIZUR®, SEQ ID NO: 7); a variant of porcine BDD-FVIII, sequence derived from GenBank Nucleotide Accession No. NM_214167.2, but with an artificial 14 amino acid linker derived from the human FVIII B-domain designed to replace the porcine FVIII full-length B-domain (SEQ ID NO: 8); porcine BDD-FVIII, sequence derived from GenBank Nucleotide Accession No. U49517, but with an artificial 14 amino acid linker derived from the human FVIII B-domain designed to replace the porcine FVIII full-length B-domain (SEQ ID NO: 9), and canine BDD-FVIII sequence derived from GenBank Nucleotide Accession No. AF049489.1, but with an artificial 14 amino acid linker derived from the human B-domain, and designed to replace the canine FVIII full-length B-domain (SEQ ID NO: 10). The use of porcine and canine (and even other mammalian FVIIIs in addition to human) are contemplated here. Porcine FVIII is currently used as a treatment for patients with acquired hemophilia A. Porcine and canine FVIII molecules, or hybrids thereof, have been evaluated and considered as alternative treatments in patients with congenital hemophilia, or hemophilia with inhibitors. By creating expression cassettes encoding porcine or canine FVIII, with a shortened B-domain linker in the presence of wild-type, truncated and/or mutated vWF, can yield large amounts of FVIII product according to the present invention; in addition, such porcine and canine FVIIIs, or hybrids thereof, may have higher catalytic activity and thus smaller amounts of FVIII may be needed in treatment scenarios.

The present invention provides recombinant expression vectors for expression FVIII and truncated vWF-Fc, and host cells transformed with the expression vectors. Any suitable expression system may be employed. The vector comprises a first and a second DNA sequence encoding FVIII and truncated vWF-Fc proteins, respectively, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the encoding DNA sequence. Thus, a promoter nucleotide sequence is operably linked to the encoding DNA sequence if the promoter nucleotide sequence controls the transcription of the encoding DNA sequence. The ability to replicate in the desired host cells, usually conferred by an origin of replication, and a selection gene by which transformants are identified, may additionally be incorporated into the expression vector.

In one embodiment, DNA sequences encoding appropriate signal peptides that may or may not be native to the FVIII or vWF can be incorporated into expression vectors. A signal peptide (also known as a leader peptide or a signal sequence) is a short peptide (typically 16-30 amino acids long) present at the N-terminus of the newly synthesized proteins that are destined towards the secretory pathway. For example, a DNA sequence for a signal peptide (secretory leader) may be provided in frame to the first sequence so that the expressed polypeptide is initially translated as a fusion protein comprising the signal peptide. A signal peptide that is functional in the intended host cells enhances extracellular secretion of the polypeptide. In some embodiments, the signal peptide is cleaved from the polypeptide upon secretion of the polypeptide from the cell. Appropriate signal peptides that are native or not native to the amino acid sequence can also be used in the present invention.

To improve the secretion of human FVIII protein, the first polynucleotide preferably includes a signal sequence before the FVIII sequence. Any signal sequence that facilitates the secretion of FVIII is suitable for the present invention. For example, the signal sequence is a wild-type human FVIII signal sequence MQIELSTCFFLCLLRFCFS (SEQ ID NO: 11).

To improve the secretion of porcine FVIII proteins, the first polynucleotide preferably includes a signal sequence before the FVIII sequence. Any signal sequence that facilitates the secretion of FVIII is suitable for the present invention. For example, the signal sequence is a wild-type Porcine VFIII signal sequence MQLELSTCVFLCLLPLGFS (SEQ ID NO: 12).

To improve the secretion of canine FVIII protein, the first polynucleotide preferably includes a signal sequence before the FVIII sequence. Any signal sequence that facilitates the secretion of FVIII is suitable for the present invention. For example, the signal sequence is a wild-type canine VFIII signal sequence MQVELYTCCFLCLLPFSLS (SEQ ID NO: 13).

To improve the secretion of truncated vWF-Fc protein, the second polynucleotide preferably includes a signal sequence before the vWF sequence. Any signal sequence that facilitates the secretion of truncated vWF-Fc is suitable for the present invention. For example, the signal sequence is a wild-type human vWF signal sequence MIPARFAGVLLALALILPGTLC (SEQ ID NO: 14).

Suitable host cells for co-expression of the polypeptides of the present invention include prokaryotes, yeast, filamentous fungi, or higher eukaryotic cells. Appropriate cloning and expression vectors for use with bacterial, fungal, yeast, and mammalian cellular hosts are well-known, for example, described in Pouwels et al. in Cloning Vectors: A Laboratory Manual, Elsevier, New York, (1985).

Suitable eukaryotic promoters for mammalian expression include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In some embodiments, a vector construct can be introduced into the cultured host cell by calcium phosphate transfection, DEAE-dextran mediated transfection, cationic lipid-mediated transfection, electroporation, transduction, infection or other methods. Such methods are described in many standard laboratory manuals.

Transcriptional and translational control sequences for mammalian host cell expression vectors may derive from viral genomes. Suitable promoter sequences and enhancer sequences for the present invention can be derived from cytomegalovirus (CMV), Polyoma virus, Adenovirus 2, Simian Virus 40 (SV40). DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication.

Sequences encoding selectable markers can be included in the DNA construct. Selectable markers for mammalian cells are known in the art, which include, glutamine synthetase, thymidine kinase, dihydrofolate reductase, aminoglycoside phosphotransferase, hygromycin B phosphotransferase, asparagine synthetase, adenosine deaminase, metallothionien, and antibiotic resistant genes such as neomycin.

The present invention comprises four major improvements related to high expression and purification of recombinant human FVIII, and its modified binding partner protein, in this case, truncated, recombinant human von Willebrand factor (vWF), in mammalian cells, namely, 1) co-expression of rec-FVIII and truncated vWF-Fc from independent promoters on a single mammalian expression vector to yield high levels of expression of both proteins through the control of optimal expression ratio of these two molecules; 2) implementation of mutations into variants of truncated human vWF to provide enhanced purification of recombinant FVIII-vWF-Fc complexes by creating smaller (i.e., monomer, dimer, or short oligomer) binding complexes compared to wild-type forms (multimers); 3) introduction of a substantial modification of the mutated von Willebrand molecule, namely, deletion of the propeptide region, that will significantly increase its expression, by eliminating the need for cleavage by certain, limiting, endogenous proteases; and 4) stabilization of the FVIII molecule in cell culture, storage in vitro, and during methods to achieve inactivation of mammalian viruses.

The combination of the elements described above results in great improvements in expression of FVIII, in greater purification of expressed protein with less loss of material, and reduced host cell protein in the final product, and also during solvent/detergent steps during inactivation of potential viruses present. These combined elements greatly improve the quality and quantity of recombinant FVIII available to patients.

Figure 1C:
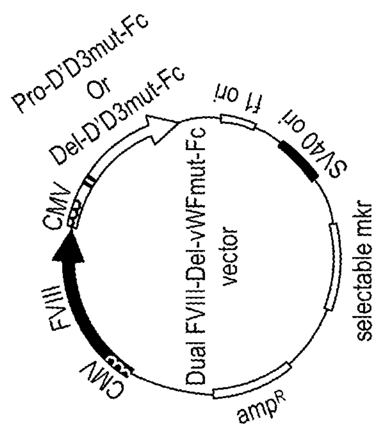
Figure 1A:
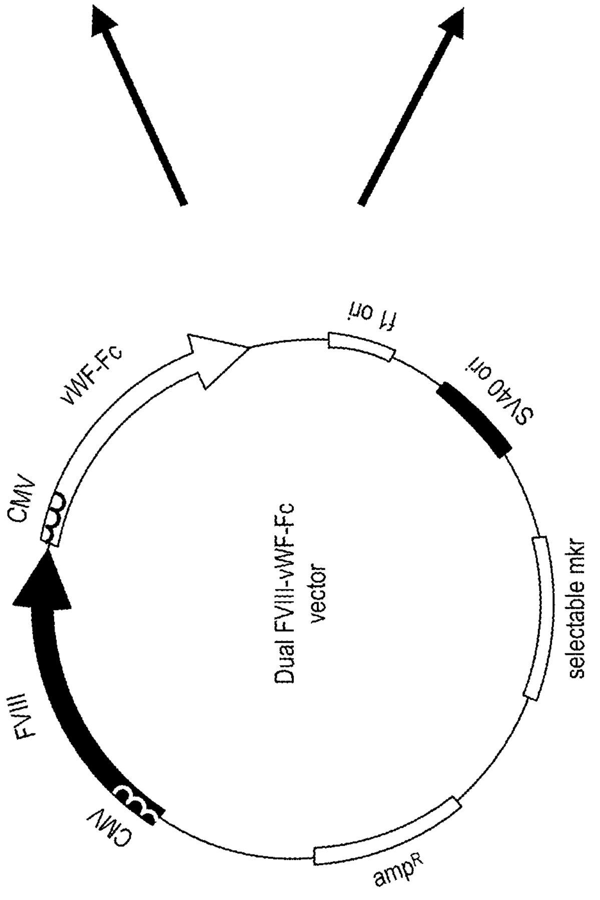

The overall method of synthesis, assembly, or process of the present invention is outlined below. FVIII and truncated vWF-Fc mutants are synthesized and cloned in tandem into a single expression vector that comprises two independent expression cassettes driven by mammalian promoters and terminated with mammalian polyadenylation signals (FIG. 1). Transfected cells are selected using antibiotic (e.g. Geneticin) or metabolic (e.g., glutamine synthetase) gene products, and then further selected and analyzed for optimal FVIII and vWF expression.

Creation of truncated vWF-Fc variants such as Pro-D'D3-Fc, Pro-D'D3mut-Fc, as well as the equivalent forms that specifically lack the propeptide domain with or without mutations, namely, Del-D'D3-Fc and Del-D'D3mut-Fc, are performed by gene synthesis of the desired DNA segments.

The FVIII-vWF complex may be removed from media by conventional chromatographic methods including absorption onto charge matrices, and/or by affinity or pseudo-affinity chromatography, for example protein A chromatography. FVIII can then be further purified away from the FVIII-vWF complex by using a FVIIISelect chromatography resin, and selective washing steps, to yield an enriched population of FVIII molecules, minimally contaminated by vWF.

The overall method for preparing FVIII is summarized as follows:

1) Transfection of cells with the co-expression plasmid containing BDD-FVIII and mutated/modified D'D3 vWF-Fc gene cassettes.
2) Identification of cells optimally expressing FVIII.
3) Recovery of secreted cell supernatant by separation of cell mass from culture medium.
4) Preparation of recovered cell medium into desired buffer for application to a column matrix that selects FVIII-vWF-Fc complexes (for example, binding to immobilized Protein A column (preferred), anti-vWF affinity matrix, or an ion exchange column).
5) The retained or eluted FVIII is further purified with a second column (for example, a camelid anti-FVIII antibody column, affinity ligand, or other affinity matrix) to remove any residual vWF-Fc and cell proteins which were not removed in step 4; it is clear that the order of removal may be reversed (steps 4 and 5), as needed, utilizing either direct (via anti-FVIII) or indirect (via anti-vWF or vWF-Fc) binding matrices.
6) FVIII can be further purified and polished by additional chromatographic steps, as necessary, including ion exchange column and nanofiltration.

The sequence identifiers for the corresponding encoded amino acid sequences are shown in Table 1.

TABLE 1

| Sequence Identifiers | Amino Acid Sequences | Origin |
|---|---|---|
| Del-D'D3mut | SEQ ID NO: 1 | Human |
| Pro-D'D3mut | SEQ ID NO: 2 | Human |
| Del-D'D3 | SEQ ID NO: 3 | Human |
| Pro-D'D3 | SEQ ID NO: 4 | Human |
| IgG-Fc | SEQ ID NO: 5 | Human |
| FVIII (BDD) | SEQ ID NO: 6 | Human |
| FVIII (BDD), OBIZUR | SEQ ID NO: 7 | Porcine |
| FVIII (BDD), porcine + 14 human amino acid linker | SEQ ID NO: 8 | Porcine |
| FVIII (BDD), porcine + 14 human amino acid linker | SEQ ID NO: 9 | Porcine |
| FVIII (BDD), canine + 14 human amino acid linker | SEQ ID NO: 10 | Canine |
| Signal sequence (wt. FVIII) | SEQ ID NO: 11 | Human |
| Signal sequence (wt. FVIII) | SEQ ID NO: 12 | Porcine |
| Signal sequence (wt. FVIII) | SEQ ID NO: 13 | Canine |
| Signal sequence (wt vWF) | SEQ ID NO: 14 | Human |
| Del-D'D3mut-Fc | SEQ ID NO: 15 | Human |
| Pro-D'D3mut-Fc | SEQ ID NO: 16 | Human |
| Del-D'D3-Fc | SEQ ID NO: 17 | Human |
| Pro-D'D3-Fc | SEQ ID NO: 18 | Human |

The following examples further illustrate the present invention. These examples are intended merely to be illustrative of the present invention and are not to be construed as being limiting.

EXAMPLES

Example 1. Construction of Co-Expression Vectors for Truncated vWF-Fc and FVIII Polypeptides Four truncated vWF-Fc DNA cassettes, each having a nucleotide sequence that encodes a truncated vWF-Fc fusion protein, were commercially synthesized (GenScript, Piscataway, N.J.). The four truncated vWF-Fc DNA cassettes are defined as follows.

(a) Pro-D'D3-Fc (D1/D2/D'/D3-Fc) represents a construct that contains vWF propeptide domain (D1D2, amino acids+ 1-741 of the wild-type vWF molecule, GenBank NM_000552) and domains D'D3 (amino acids 742-1247 of the wild-type vWF molecule), fused at its C-terminus with an immunoglobulin Fc domain derived from human $IgG_1$ (e.g., UniProtKB 01857, amino acids 104-330).

(b) Del-D'D3-Fc (D'/D3-Fc) represents a construct that contains vWF domains D'D3, fused at its C-terminus with an immunoglobulin Fc domain; in contrast to construct (a), the propeptide domain (D1D2) has been deleted.

(c) Pro-D'D3mut-Fc (D1/D2/D'/D3+mutation-Fc) represents a construct similar to (a), except having mutations at C1099 and C1142 of the complete vWF molecule (including its signal sequence). C1099 and C1142 are from an old and recognized naming convention from the Human Genome Variation Society, where the amino acid counting starts from the signal sequence of the complete vWF molecule; when counting starts from the D' domain, the equivalent mutations are C336 and C379.

(d) Del-D'D3mut-Fc (D'/D3+mutation) represents a construct similar to (b) except having mutations at C1099 and C1142 of the complete vWF molecule (including its signal sequence, with nomenclature according to HGVS numbering convention).

DNA encoding the human FVIII B-domain deleted protein (BDD FVIII) was also commercially synthesized (Genewiz, South Plainfield, N.J.).

Nucleotide sequences encoding for each protein listed in Table 1 were codon-optimized using algorithms that account for enhanced heterologous expression Chinese Hamster Ovary (CHO) cells. The DNA sequence that encodes the signal peptide for each protein was also codon-optimized.

The truncated vWF-Fc and BDD FVIII cDNAs were each subcloned into a DNA plasmid expression vector through cloning sites BsiWI and Fsp I on the plasmid (FIG. 1), where ‘CMV’ is a cytomegalovirus promoter sequence, represented by a white squiggle line for FVIII and black squiggle line for vWF-Fc; is a FVIII gene sequence (BDD FVIII); ‘vWF-Fc’ is a generic name for any vWF-Fc variant described above, including Pro-D'D3-Fc, Del-D'D3-Fc, Pro-D'D3mut-Fc and Del-D'D3mut-Fc; ‘ampR’ is an ampicillin-resistance gene; ‘selectable mkr’ is a selectable marker for specifically isolating cells that carry the desired plasmid (e.g. glutamine synthetase, G418); ‘SV40 ori’ is the sequence of mammalian simian virus that contains an origin of replication (for replication in mammalian cells); f1 ori' is the sequence of bacteriophage f1 that contains an origin of replication (for replication in bacteria cells).

Since dimerization of vWF fragment is important for its interaction with FVIII, the DNA sequence encoding the Fc fragment was introduced to the C-terminus of truncated vWF fragment to direct truncated vWF dimer formation. In addition, since highly-expressed, wild-type vWF, despite the fact that it is truncated in the present invention, may form aggregates due to its extensive multimerization, and thus complicate FVIII and purification, two mutations were introduced at amino acid positions C1099 and C1142 (including signal sequence; HGVS numbering convention), or C336 and C379 (counting starting from D' in the vWF D'D3 domain). These two sites are involved in vWF multimer formation and thus introducing mutations at these sites block vWF multimer formation, simplify purification, and create a better quality of FVIII than current methods.

Example 2. Co-Expression of Human BDD FVIII and Truncated vWF-Fc in CHO Mammalian Cell Lines CHO cells were cultured in CD-CHO medium (Thermo Fisher Scientific, Waltham, Mass.) and prepared for electroporation. Cells were seeded at $0.3\times10^6$ cells/mL in E125 (125 ml) shaker flasks (SF) and incubated in $CO_2$ shaker incubator. Cells were sub-cultured when the cell density reached $1.5\text{-}3.0\times10^6$ cells/mL; at cell passage 3 (P3), electroporation was performed. On the day of the electroporation, 100 μl transfection solution (Nucleofector Kit V Solution, Lonza, Walkersville, Md.) containing 5 μg of linearized expression vector of Example 1 was used to suspend $3\times10^6$ cells (early log phase). The cell/DNA mixture was then transferred to the cuvette of a Nucleofector 2b electroporation device, and program U-24 (Lonza) was used to electroporate the DNA into the cells. After electroporation, the cells were immediately transferred into the 24-well plate containing pre-warmed CD-CHO medium (without drug selection) and incubated in a humidified environment at 37° C. with 5% $CO_2$. After 24-hour incubation, the post-electroporation cells were plated into 96-well microplates at a density of 3000 cells/well in CD-CHO medium containing 25 μM L-methionine sulfoximine (MSX) and incubated for 2-3 weeks at 37° C. with 95% humidity and 5% $CO_2$. The successfully-transfected cell colonies were seen after 2-3 weeks incubation and the FVIII-expressing cells were selected using a one-stage clotting assay of the supernatant. Selected cell pools were then gradually expanded from 96-well plates to 6-well plates, and eventually to shaker flasks, for suspension culture. The selected cell pools were then subjected to limited dilution cloning at a cell density of 0.3 cell/well. FVIII expression levels in excess of 1000 IU/ml in a 1 L shake flask were determined with a one-stage clotting assay.

Example 3. FVIII Protein Expression and Purification

Once FVIII-expressing cell pools were obtained, the FVIII expression level was tested in fed-batch culture. Cells expressing both FVIII and truncate vWF-Fc variants were first adapted into ActiPro medium (Hyclone, Salt Lake City, Utah) and seeded at a cell density of $1\times10^6$/ml. When the cell density reached $6\times10^6$ cells/ml, Cell Boost 7a/7b Supplement (Hyclone) was added every other day according to the manufacture’s recommendation. The cell density and the FVIII activity were checked regularly to monitor the cell growth and FVIII expression. After 14-days, the fed-batch culture was terminated, and the cell culture supernatant was collected by centrifuging the cell culture medium at 100×g, and stored in −80° C. freezer.

Figure 7B:
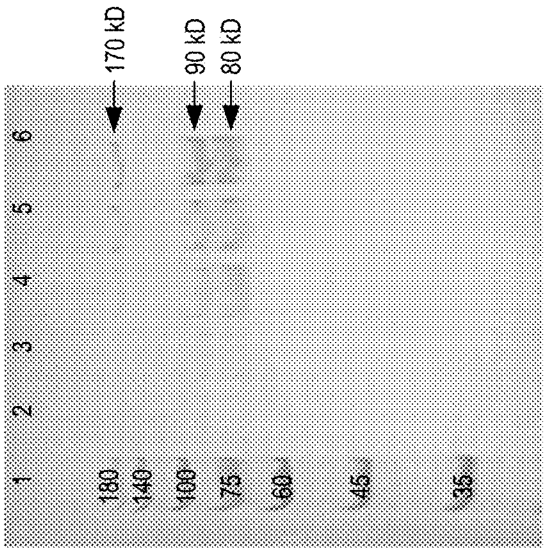
FIGS. 7A-7B demonstrate the purity of FVIII expressed with Del-D'D3mut-Fc and purified by affinity chromatography. (7A) A gel electropherogram of recombinantly-expressed FVIII obtained by purification, and (7B) a corresponding Western Blot for the protein lanes in (7A). An anti-human FVIII antibody was used to detect the protein in the Western blot. Lane 1, Molecular weight marker (MW); Lane 2, starting material from cell supernatants; Lane 3, flow-through material after Protein A chromatography; Lane 4, 0.3 M $CaCl_2$ elution fraction from a Protein A affinity column; Lane 5, 50% ethylene glycol elution of material from FVIIISelect affinity resin column; Lane 6, commercial protein BDD-FVIII (Xyntha®). Arrows indicate the three expected BDD-FVIII protein bands corresponding to approximately 170, 90 and 80 kilodaltons (kD).
Figure 7A:
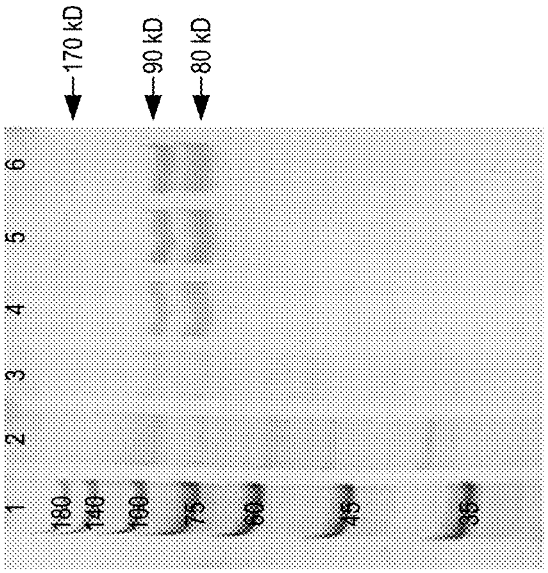

For FVIII purification, the clarified supernatant was further processed with high-speed centrifugation, then filtered through 0.45 μm filter. The supernatant was mixed with an equal volume of dilution buffer (40 mM Tris-HCl, pH 7.0, 150 mM NaCl). Using the AKTA Pure chromatography system, the diluted supernatant was loaded onto a HiTrap MabSelect PrismA column, and the column was then washed with 10 column volumes (CV) of wash buffer (20 mM Tris-HCl, pH 7.0, 150 mM NaCl). A FVIIISelect affinity ligand column (GE Healthcare) was connected in series with the Protein A column outlet. The elution buffer (20 mM Tris-HCl, pH 7.0, 0.3 M $CaCl_2$) was applied to the protein A column to separate the FVIII from bound vWF-Fc fusion complex. After washing, the connected column series were separated and FVIII elution buffer (20 mM histidine, 20 mM $CaCl_2$, 1.5 M NaCl and 0.02% Tween-80 in 50% ethylene glycol, pH 6.5) was used to elute the FVIII from the FVIIISelect column. The purified BDD-FVIII was then buffer exchanged into 0.3% (w/v) sucrose, 2.2% (w/v) glycine, 20 mM histidine, 220 mM NaCl, 25 mM $CaCl_2$ and 0.008% Tween-80, pH 6.9 for further protein characterization. The FVIII purification intermediate and final product are shown on lanes 4-6 of an SDS-PAGE gel (FIG. 7A) and corresponding Western Blot (FIG. 7B).

Example 4. Truncated vWF-Fc Dimer and Multimer Form Analysis

Figure 8:
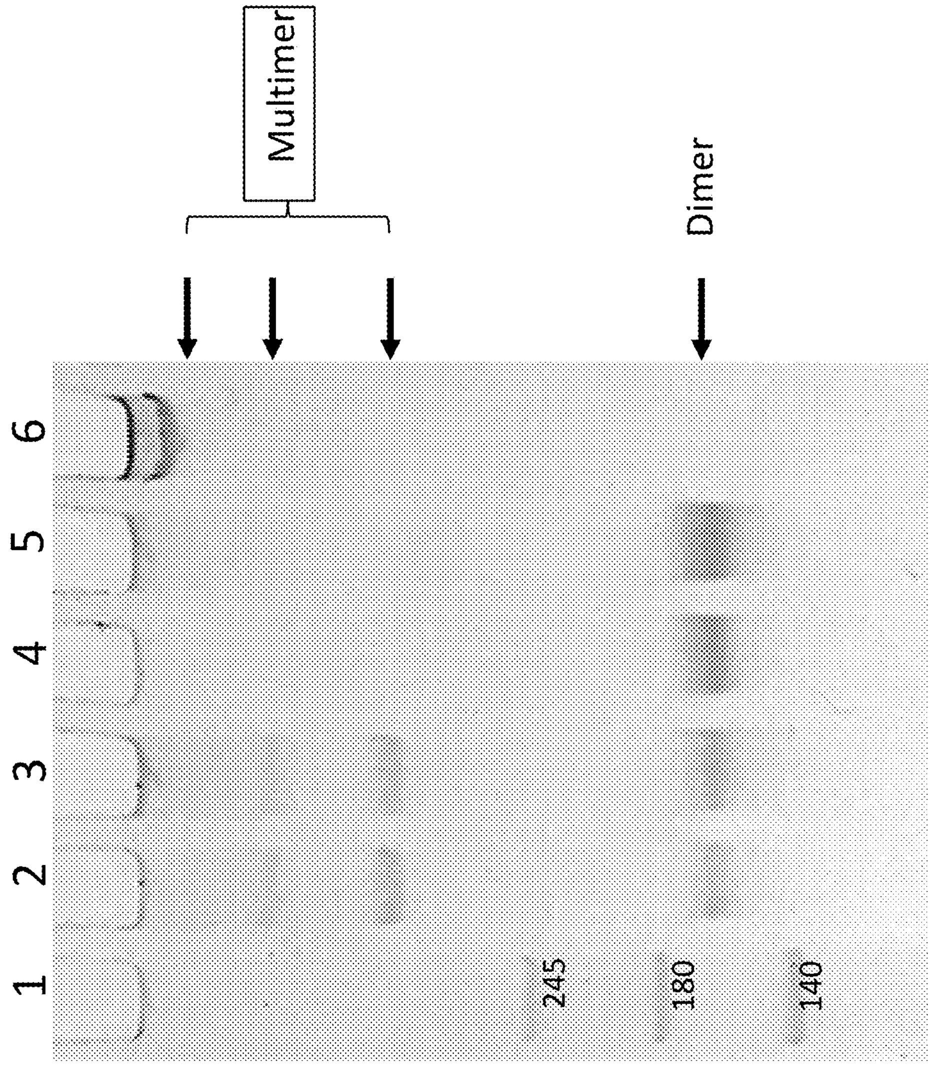
FIG. 8 shows the expression of truncated vWF-Fc dimers and multimers. Protein A-purified, truncated vWF-Fc variants including Pro-D'D3-Fc (Lane 2); Del-D'D3-Fc (Lane 3), Pro-D'D3mut-Fc (Lane 4) and Del-D'D3mut-Fc (Lane 5) were compared with plasma-derived full-length vWF protein (Lane 6) by non-reducing PAGE. The high molecular weight bands (>180 kD, arrows) in lanes 2 and 3 represent truncated vWF-Fc multimers. Since the mutations at C1099 and C1142 interrupt multimer formation, the Pro-D'D3mut-Fc (Lane 4) and Del-D'D3mut-Fc (Lane 5) only formed dimers (~160 kD; arrows).

Four recombinant truncated vWF-Fc polypeptide constructs were evaluated for their ability to form dimers or high molecular weight complexes (i.e., multimers) by electrophoretic analysis on a non-reducing 4% SDS-PAGE gel. After electrophoresis, the gel was stained with Coomassie Brilliant Blue (FIG. 8). The results indicated that the vWF-Fc variants, Pro-D'D3-Fc (Lane 2) and Del-D'D3-Fc (Lane 3), both formed dimers of about 160 kD) and multimers (>180 kD), while the vWF-Fc variants that contain mutations, Pro-D'D3mut-Fc (Lane 4) and Del-D'D3mut-Fc (Lane 5), only formed dimers of ca. 160 kD, due to the mutations that block multimer formation.

Example 5. Characterization of Truncated vWF-Fc Polypeptide Binding Affinity to B-Domain-Deleted (BDD)-FVIII Recombinant protein constructs, corresponding to each of the truncated vWF-Fc variants, were expressed in CHO-K1 cells, and proteins were purified from supernatant using Protein A affinity chromatography. To characterize their respective FVIII binding affinities, equimolar amounts of the vWF-Fc variants were prepared in TBST buffer (20 mM Tris, pH 7.6, 150 mM NaCl, 0.1% Tween-20) and directly coated onto 96-well microplates overnight at 4° C. After coating, plates were blocked with TBST-3% bovine serum albumin (BSA) buffer for 2 hours at room temperature (RT) and then incubated with increasing concentrations (0-4000 pM) of recombinant FVIII (Prospec Bio, East Brunswick, N.J.) for 1 hour at room temperature (RT). After equilibration and washing, bound FVIII was detected with a sheep anti-FVIII polyclonal antibody, followed by a secondary antibody against sheep IgG, that itself was conjugated to horseradish peroxidase. Blank values were subtracted from the absorbance measurements. The assay was performed in triplicates. The analysis of the binding assay showed that all four vWF-Fc fragments bound to recombinant BDD-FVIII with similar apparent affinity constants (about 500 pM) that is comparable to the binding affinity of full-length plasma-derived vWF to BDD-FVIII (Shiltagh et al., Blood, vol. 123, p. 4143-4151, 2014).

Example 6. vWF Variant D'D3mut-Fc Improves the FVIII Purification Recovery Rate As discussed above, mature, wild-type Pro-D'D3-Fc fusion protein results in multimer formation, and possibly protein aggregation, through the N-terminal disulfide bonds mediated by D3 domains, and C-terminal dimerization mediated by Fc domains. Such aggregation interferes with vWF-Fc binding to an Fc affinity matrix, like Protein A; in addition, FVIII elution from the FVIII/vWF-Fc complex is compromised by aggregate formation. By introducing mutations at amino acids C1099 and C1142, multimer assembly is interrupted, while dimer formation is promoted, thus leading to uniform vWF-Fc dimer formation. Therefore, both FVIII capture (in the form of a FVIII/vWF-Fc complex) on Protein A matrix, and FVIII elution (from the captured FVIII/vWF-Fc complex), are improved.

The cell-culture medium from transfected cells co-expressing FVIII and either Pro-D'D3-Fc or Del-D'D3mut-Fc were purified using Protein A chromatography; the FVIII-vWF purification recovery rates are summarized in Table 2. The results show that the FVIII-vWF purification recovery rate is markedly higher when FVIII is co-expressed with Del-D'D3mut-Fc than FVIII is co-expressed with Pro-D'D3-Fc fusion (87% vs 64%). In addition, high column back-pressure was consistently observed during the FVIII purification using the Pro-D'D3-Fc variant, possibly due to the presence of high numbers of high-molecular weight multimers.

TABLE 2

| Protein Expression | Purification | FVIII Recovery Rate |
|---|---|---|
| FVIII/Pro-D'D3-Fc | Protein A Chromatography | 64% |
| FVIII/ Del-D'D3mut-Fc | Protein A Chromatography | 87% |

Example 7. Recombinant Truncated vWF-Fc Variants Enhance the Soluble FVIII Expression It has been suggested that 90% of the BDD-FVIII is bound to cell membrane when it is expressed alone in cell system; the reason for this is unknown (Kolind et al, J. Biotech., 2011, 151, pp. 357-362). This phenomenon may be explained as naturally the FVIII molecule is present in a non-covalent complex with, and circulates with, vWF in plasma, which blocked FVIII interaction with the cell membrane To test whether co-expression of the truncated vWF-Fc fusion protein could increase recombinant FVIII expression, four purified vWF-Fc variants (Pro-D'D3-Fc, Pro-D'D3muts-Fc, Del-D'D3mut-Fc and Del-D'D3-Fc proteins), plasma vWF, and a negative control protein (HSA) were included in the assay.

Figure 9:
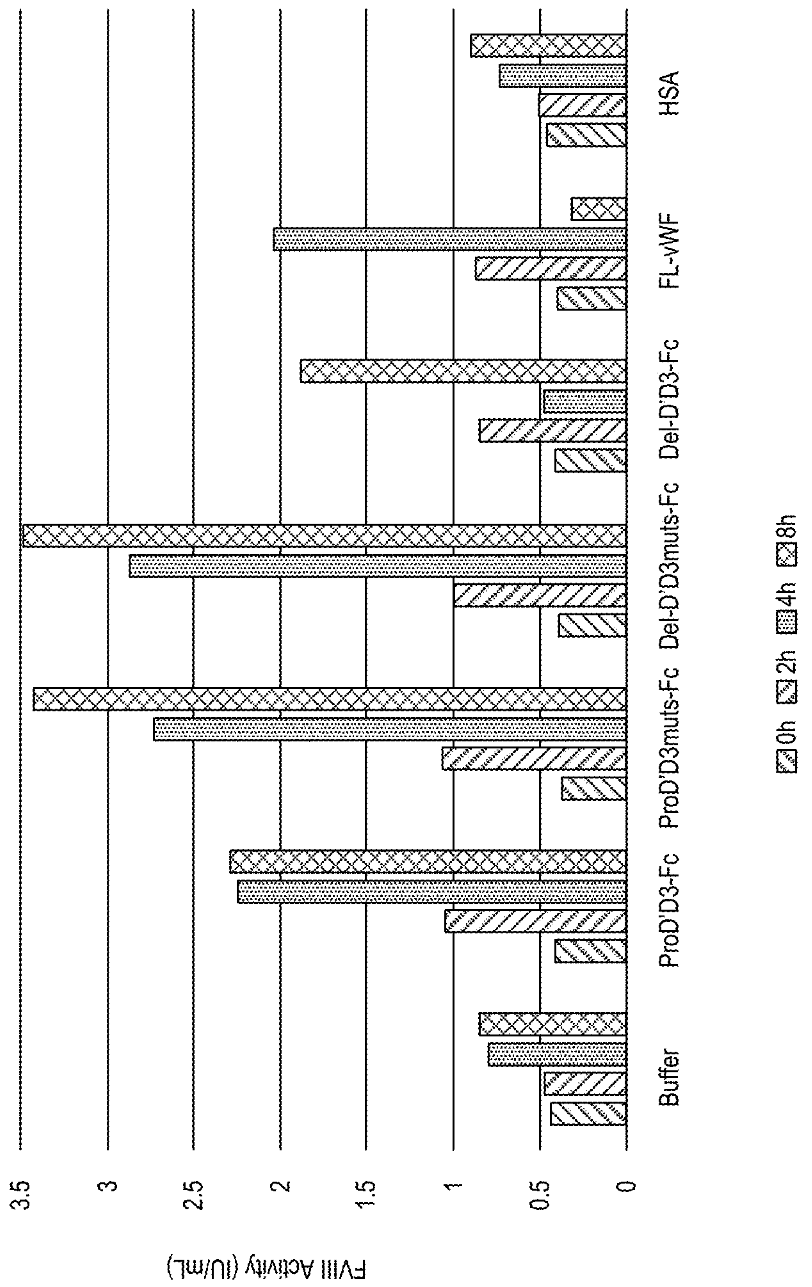
FIG. 9 demonstrates the protective effects of truncated vWF-Fc fusion proteins on recombinant FVIII protein expression. Truncated vWF-Fc fusion proteins, including wild-type Pro-D'D3-Fc, Del-D'D3-Fc, as well as Pro-D'D3mut-Fc and Del-D'D3mut-Fc proteins and plasma-derived vWF (negative control protein, human serum albumin (HSA), were tested by addition of equimolar amounts of variant (or HSA) with cells expressing only FVIII. FVIII activity was determined using a one-stage clotting assay, with samples removed for testing at timed intervals, between 0 and 8 hours.

The four truncated recombinant vWF-Fc variants were expressed in CHO cells and purified with Protein A chromatography. To demonstrate that truncated vWF-Fc variants, co-expressed with BDD-FVIII, would increase the BDD-FVIII yield in cell culture by shielding BDD-FVIII from cell binding, equal masses of each of the four-recombinant truncated vWF-Fc variants, as well as full-length plasma-derived vWF (FL-vWF), were added to the supernatant of the cell line that expresses only BDD-FVIII; human serum albumin (HSA) was added as a negative control. FVIII activities of the cell culture supernatants were tested every 2 hours using a one-stage clotting assay for each sample. The results demonstrated that all four truncated vWF-Fc variants, as well as the plasma-derived, full-length vWF, can substantially increase FVIII yield in cell culture. Unexpectedly, the Del-D'D3mut-Fc fusion demonstrated the highest effect on FVIII expression (FIG. 9). Cells expressing only FVIII, or cell cultures to which HSA was added, did not show detectable increase in FVIII activity.

Example 8. Co-Expression of Truncated vWF-Fc Fragments (Del-D'D3mut-Fc) with Human FVIII Completely Blocked the FVIII Binding to Cell Membrane It has been recognized that B-domain-deleted FVIII significantly interacts with cell membranes during recombinant protein production, thereby lowering its apparent expression in cell culture.

To confirm this observation, cell culture medium from cells expressing only human BDD-FVIII were treated with 0.5 M NaCl (salt ions provide charge shielding/electrical double layer on the charged protein to modulate the non-specific protein-surface interaction) for 5 min at room temperature and then centrifuged to harvest the supernatant. FVIII coagulation activity was measured using a one-stage clotting assay for both NaCl-treated and non-treated supernatant. The results showed that as much as 90% of secreted BDD-FVIII was bound to the cells. By contrast, when FVIII is co-expressed with vWF-Fc variant, Del-D'D3mut-Fc, addition of NaCl did not increase the cell culture supernatant FVIII activity, suggesting that the Del-D'D3mut-Fc completely blocked FVIII binding to the cell membrane, resulting in almost 100% secreted recombinant BDD-FVIII being released into the cell culture supernatant.

Example 9. Recombinant Truncated vWF-Fc Variant (Del-D'D3mut-Fc) Enhanced the In Vitro Stability of FVIII in Cell Culture Literature indicates that recombinant BDD-FVIII has poor in vitro stability in cell culture medium at room temperature (RT).

Figure 10:
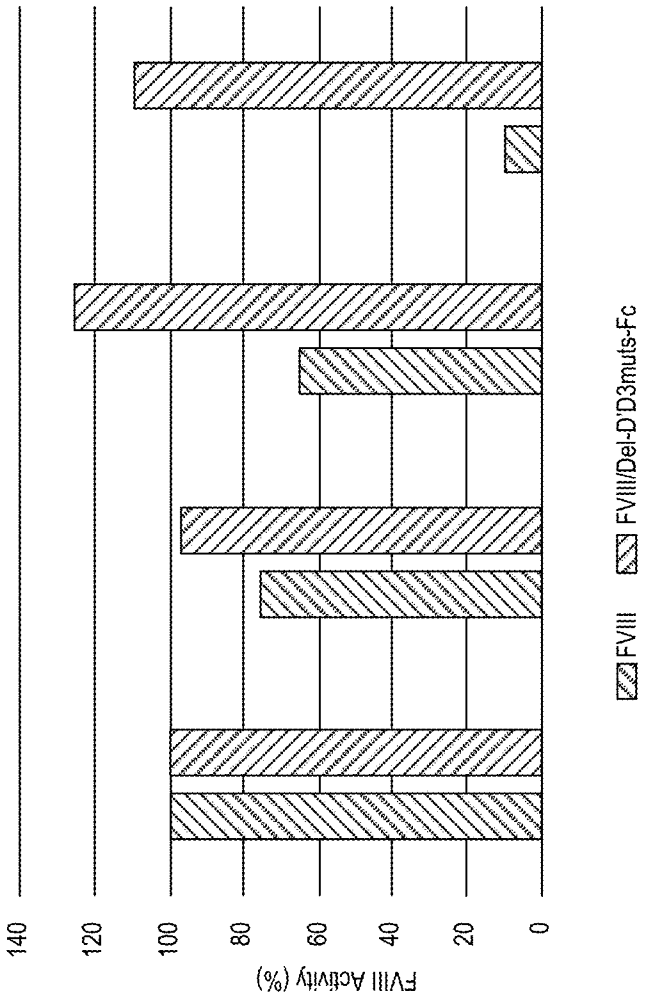
FIG. 10 illustrates that co-expression of truncated vWF-Fc with FVIII considerably improved the in vitro stability of FVIII in cell culture. Samples of cell culture media containing either FVIII, or FVIII/Del-D'D3mut-Fc complexes, were maintained at room temperature over a 24-hour period, with sampling at 0, 4, 8, and 24 hours. Stability was assessed as a function of FVIII activity in a one-stage clotting assay.

To determine if co-expression with vWF could increase the FVIII stability in cell culture, the stability of FVIII expressed either alone in cell culture, or co-expressed with Del-D'D3mut-Fc variant, was evaluated. Samples of cell culture media containing either FVIII or FVIII-Del-D'D3mut-Fc complex were tested at room temperature, and the FVIII activity were measured using a one-stage clotting assay at timed intervals (0, 4, 8, and 24 hours) for each sample. The results showed that, unexpectedly, FVIII, co-expressed with the Del-D'D3mut-Fc vWF variant, could maintain its activity unchanged for at least 24 hours at room temperature (FIG. 10). Without the co-expression with this vWF-Fc variant, FVIII was not stable, and nearly 90% of its activity was lost at 24 hours (FIG. 10).

Figure 11:
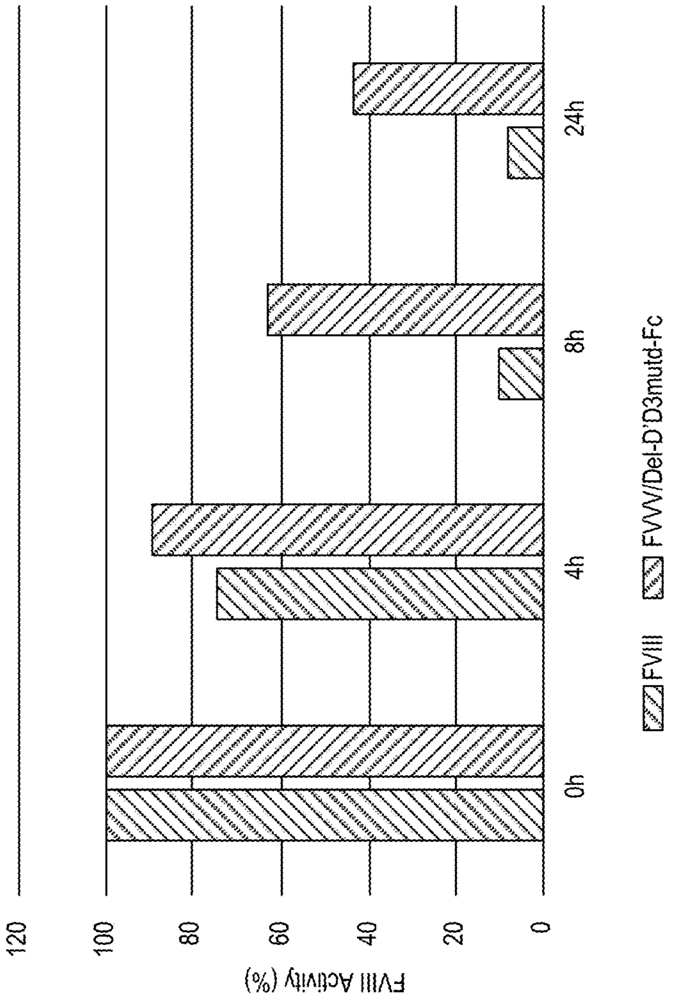
FIG. 11 demonstrates that co-expression of truncated vWF-Fc with FVIII improved recombinant FVIII stability during a solvent-detergent viral inactivation procedure. Cell cultures expressing either recombinant BDD-FVIII only, or BDD-FVIII co-expressed with Del-D'D3mut-Fc vWF variant, were treated with viral inactivation reagents (i.e, TNBP and Triton-X-100) for 24 hours, and the FVIII coagulation activity were monitored by a one-stage clotting assay at 0, 4, 8, and 24 hours timepoints.

Example 10. Co-Expression of Truncated vWF-Fc Variant (Del-D'D3mut-Fc) Stabilized the Recombinant FVIII During the Virus Inactivation Procedure Cell cultures expressing only recombinant BDD-FVIII and cell cultures containing the BDD-FVIII co-expressed with Del-D'D3mut-Fc vWF variant were treated with the virus inactivation reagents (1% Triton X-100 and 0.3% Tri (n-butyl) phosphate) for 24 hours. The FVIII coagulation activity were monitored with one-stage clotting assay at timed intervals (0, 4, 8, and 24 hours after treating with inactivation reagent) for each sample. The results indicated that cell cultures expressing FVIII alone lost almost 90% of its activity after 8 hours of virus inactivation treatment. In contrast, the FVIII activity of the FVIII-vWF-Fc-expressing cell culture only lost about 40% during the same time period. The results indicated that the co-expressed vWF-Fc variant substantially stabilized the FVIII activation during the virus inactivation process (FIG. 11). This indicates that the Del-D'D3mut-Fc variant is remarkably stable under these conditions.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A vector comprising:

(a) a first polynucleotide sequence encoding a B-domain-deleted factor VIII protein (FVIII), operably linked to a first promoter, and (b) a second polynucleotide sequence encoding a fusion protein comprising a truncated von Willebrand factor (vWF) and an immunoglobulin Fc fused to the C-terminal of the truncated vWF, operably linked to a second promoter, wherein the truncated vWF comprises the amino acid sequence of SEQ ID NO: 1, SEQ ID NO: 2, SEQ ID NO: 3, or SEQ ID NO: 4, or having 95% amino acid sequence identity thereof.

2. The vector according to claim 1, wherein the truncated vWF comprises the amino acid sequence of SEQ ID NO: 1, or having 95% amino acid sequence identity thereof, provided that the amino acid residues 336 and 379 are not cysteine.

3. The vector according to claim 2, wherein the truncated vWF comprises the amino acid sequence of SEQ ID NO: 1.

4. The vector according to claim 1, wherein the truncated vWF comprises the amino acid sequence of SEQ ID NO: 2, or having 95% amino acid sequence identity thereof, provided that the amino acid residues 1077 and 1020 are not cysteine.

5. The vector according to claim 4, wherein the truncated vWF comprises the amino acid sequence of SEQ ID NO: 2.

6. The vector according to claim 1, wherein the B-domain deleted FVIII has the amino acid sequence of SEQ ID NO: 6, 7, 8, 9, or 10, or having 95% amino acid sequence identity thereof.

7. The vector according to claim 6, wherein the B-domain-deleted FVIII has the amino acid sequence of SEQ ID NO: 6, or having 95% amino acid sequence identity thereof.

8. The vector according to claim 1, wherein the first polynucleotide sequence further comprises a first signal sequence and the second polynucleotide sequence further comprises a second signal sequence.

9. An isolated host cell comprising the vector of claim 1.

10. A method for preparing FVIII, comprising the steps of:

(a) transfecting cells with a plasmid comprising the vector of claim 1, (b) selecting the cells secreting FVIII, (c) collecting the supernatant of the selected cells, and (d) purifying FVIII from the selected supernatant.

* * * * *